United States Patent
Woloszko et al.

(10) Patent No.: US 8,979,838 B2
(45) Date of Patent: Mar. 17, 2015

(54) SYMMETRIC SWITCHING ELECTRODE METHOD AND RELATED SYSTEM

(75) Inventors: Jean Woloszko, Austin, TX (US); John Goode, Austin, TX (US); Philip M. Tetzlaff, Austin, TX (US)

(73) Assignee: ArthroCare Corporation, Austin, TX (US)

( * ) Notice: Subject to any disclaimer, the term of this patent is extended or adjusted under 35 U.S.C. 154(b) by 1194 days.

(21) Appl. No.: 12/785,563

(22) Filed: May 24, 2010

(65) Prior Publication Data

US 2011/0288539 A1 Nov. 24, 2011

(51) Int. Cl.
*A61B 18/14* (2006.01)
*A61B 18/12* (2006.01)
(Continued)

(52) U.S. Cl.
CPC ........... *A61B 18/1206* (2013.01); *A61B 18/042* (2013.01); *A61B 18/148* (2013.01); *A61B 18/14* (2013.01); *A61B 2018/00178* (2013.01); *A61B 2018/0044* (2013.01); *A61B 2018/124* (2013.01); *A61B 2018/144* (2013.01); *A61B 2018/1472* (2013.01)
USPC ............................................. 606/41; 606/34

(58) Field of Classification Search
CPC ............... A61B 2018/00708; A61B 2018/144; A61B 2018/1472; A61B 2018/124; A61B 18/042; A61B 18/148
USPC .......... 606/33, 34, 41, 42, 48, 50; 607/98, 99, 607/101, 115, 154
See application file for complete search history.

(56) References Cited

U.S. PATENT DOCUMENTS

| 2,056,377 | A | 10/1939 | Wappler | 125/303 |
| 3,633,425 | A | 1/1972 | Sanford | 73/356 |
| 3,659,607 | A | 5/1972 | Banko | 606/169 |

(Continued)

FOREIGN PATENT DOCUMENTS

| DE | 3245570 | 6/1984 | ............ A61B 17/38 |
| DE | 3530335 | 3/1987 | ............ A61B 17/39 |

(Continued)

OTHER PUBLICATIONS

Barry et al., "The Effect of Radiofrequency-generated Thermal Energy on the Mechanical and Histologic Characteristics of the Arterial Wall in Vivo: Implications of Radiofrequency Angioplasty" *American Heart Journal* vol. 117, pp. 332-341, 1982.

(Continued)

*Primary Examiner* — Michael Peffley
*Assistant Examiner* — Thomas Giuliani
(74) *Attorney, Agent, or Firm* — Norman F. Hainer, Jr.

(57) ABSTRACT

Electrosurgical system and related methods that include: producing energy by a generator of an electrosurgical controller, the generator comprises a first terminal coupled to a first electrode of an electrosurgical wand, and the generator comprises a second terminal coupled to a second electrode of the electrosurgical wand; forming, responsive to the energy, a plasma proximate to the first electrode, while the second electrode acts as a return electrode; reducing energy output of the generator such that the plasma proximate the first electrode is extinguished, then producing energy from the generator with the first terminal coupled to the first electrode and the second terminal coupled to the second electrode; and forming, responsive to the energy, a plasma proximate to the second electrode, while the first electrode acts as a return electrode.

13 Claims, 9 Drawing Sheets

(51) Int. Cl.
*A61B 18/04* (2006.01)
*A61B 18/00* (2006.01)

(56) References Cited

U.S. PATENT DOCUMENTS

| | | | |
|---|---|---|---|
| 3,815,604 A | 6/1974 | O'Malley et al. | 128/305 |
| 3,828,780 A | 8/1974 | Morrison, Jr. et al. | 128/275 |
| 3,901,242 A | 8/1975 | Storz | 128/303 |
| 3,920,021 A | 11/1975 | Hiltebrandt | 128/303 |
| 3,939,839 A | 2/1976 | Curtiss | 128/303 |
| 3,970,088 A | 7/1976 | Morrison | 128/303 |
| 4,040,426 A | 8/1977 | Morrison, Jr. | 128/303 |
| 4,043,342 A | 8/1977 | Morrison, Jr. | 128/303 |
| 4,074,718 A | 2/1978 | Morrison, Jr. | 128/303 |
| 4,092,986 A | 6/1978 | Schneiderman | 128/303 |
| 4,116,198 A | 9/1978 | Roos | 128/303 |
| 4,161,950 A | 7/1979 | Doss et al. | 606/48 |
| 4,181,131 A | 1/1980 | Ogiu | 128/303 |
| 4,184,492 A | 1/1980 | Meinke et al. | 128/303 |
| 4,202,337 A | 5/1980 | Hren et al. | 128/303 |
| 4,228,800 A | 10/1980 | Degler, Jr. et al. | 128/303 |
| 4,232,676 A | 11/1980 | Herczog | 128/303 |
| 4,248,231 A | 2/1981 | Herczog et al. | 128/303 |
| 4,269,174 A | 5/1981 | Adair | 128/842 |
| 4,326,529 A | 4/1982 | Doss et al. | 128/303 |
| 4,381,007 A | 4/1983 | Doss | 128/303 |
| 4,449,926 A | 5/1984 | Weiss | 433/32 |
| 4,474,179 A | 10/1984 | Koch | 606/40 |
| 4,476,862 A | 10/1984 | Pao | 128/303 |
| 4,483,338 A | 11/1984 | Bloom et al. | 606/50 |
| 4,512,351 A | 4/1985 | Pohndorf | 607/117 |
| 4,532,924 A | 8/1985 | Auth et al. | 128/303 |
| 4,548,207 A | 10/1985 | Reimels | 128/303 |
| 4,567,890 A | 2/1986 | Ohta et al. | 128/303 |
| 4,572,214 A | 2/1986 | Nordenstrom et al. | 607/127 |
| 4,573,448 A | 3/1986 | Kambin | 606/170 |
| 4,582,057 A | 4/1986 | Auth et al. | 606/31 |
| 4,590,934 A | 5/1986 | Malis et al. | 128/303 |
| 4,593,691 A | 6/1986 | Lindstrom et al. | 128/303 |
| 4,658,817 A | 4/1987 | Hardy | 606/14 |
| 4,660,571 A | 4/1987 | Hess et al. | 128/784 |
| 4,674,499 A | 6/1987 | Pao | 128/303 |
| 4,682,596 A | 7/1987 | Bales et al. | 128/303 |
| 4,706,667 A | 11/1987 | Roos | 128/303 |
| 4,727,874 A | 3/1988 | Bowers et al. | 128/303 |
| 4,765,331 A | 8/1988 | Petruzzi et al. | 128/303 |
| 4,785,823 A | 11/1988 | Eggers et al. | 128/692 |
| 4,805,616 A | 2/1989 | Pao | 128/303 |
| 4,823,791 A | 4/1989 | D'Amelio et al. | 123/303 |
| 4,832,020 A | 5/1989 | Augustine | 128/207.14 |
| 4,832,048 A | 5/1989 | Cohen | 128/786 |
| 4,896,671 A | 1/1990 | Cunningham et al. | 600/374 |
| 4,907,589 A | 3/1990 | Cosman | 606/34 |
| 4,920,978 A | 5/1990 | Colvin | 128/784 |
| 4,931,047 A | 6/1990 | Broadwin et al. | 604/22 |
| 4,936,281 A | 6/1990 | Stasz | 128/660 |
| 4,936,301 A | 6/1990 | Rexroth et al. | 606/45 |
| 4,943,290 A | 7/1990 | Rexroth et al. | 606/45 |
| 4,958,539 A | 9/1990 | Stasz et al. | 76/104.1 |
| 4,966,597 A | 10/1990 | Cosman | 606/50 |
| 4,967,765 A | 11/1990 | Turner et al. | 128/785 |
| 4,976,709 A | 12/1990 | Sand | 606/5 |
| 4,976,711 A | 12/1990 | Parins et al. | 606/48 |
| 4,979,948 A | 12/1990 | Geddes et al. | 606/33 |
| 4,998,933 A | 3/1991 | Eggers et al. | 606/41 |
| 5,007,908 A | 4/1991 | Rydell | 606/47 |
| 5,009,656 A | 4/1991 | Reimels | 606/48 |
| 5,035,696 A | 7/1991 | Rydell | 606/47 |
| 5,047,026 A | 9/1991 | Rydell | 606/48 |
| 5,047,027 A | 9/1991 | Rydell | 606/48 |
| 5,078,717 A | 1/1992 | Parins et al. | 606/48 |
| 5,080,660 A | 1/1992 | Buelna | 606/45 |
| 5,084,044 A | 1/1992 | Quint | 606/27 |
| 5,084,045 A | 1/1992 | Helenowski | 606/32 |
| 5,085,659 A | 2/1992 | Rydell | 606/47 |
| 5,088,997 A | 2/1992 | Delahuerga et al. | 606/42 |
| 5,098,431 A | 3/1992 | Rydell | 606/48 |
| 5,099,840 A | 3/1992 | Goble | 128/422 |
| 5,102,410 A | 4/1992 | Dressel | 606/15 |
| 5,108,391 A | 4/1992 | Flachenecker et al. | 606/38 |
| RE33,925 E | 5/1992 | Bales et al. | 606/48 |
| 5,112,330 A | 5/1992 | Nishigaki et al. | 606/46 |
| 5,122,138 A | 6/1992 | Manwaring | 606/46 |
| 5,125,928 A | 6/1992 | Parins et al. | 606/48 |
| 5,137,530 A | 8/1992 | Sand | 606/5 |
| 5,156,151 A | 10/1992 | Imran | 600/375 |
| 5,158,565 A | 10/1992 | Marcadis et al. | 606/185 |
| 5,167,659 A | 12/1992 | Ohtomo et al. | 606/40 |
| 5,171,311 A | 12/1992 | Rydell et al. | 606/48 |
| 5,178,620 A | 1/1993 | Eggers et al. | 606/41 |
| 5,190,517 A | 3/1993 | Zieve et al. | 604/22 |
| 5,192,280 A | 3/1993 | Parins | 606/48 |
| 5,195,959 A | 3/1993 | Smith | 604/34 |
| 5,197,466 A | 3/1993 | Marchosky et al. | 128/399 |
| 5,197,963 A | 3/1993 | Parins | 606/46 |
| 5,201,729 A | 4/1993 | Hertzmann et al. | 606/2 |
| 5,207,675 A | 5/1993 | Canady | 606/40 |
| 5,207,684 A | 5/1993 | Nobles | 606/108 |
| 5,217,457 A | 6/1993 | Delahuerga et al. | 606/42 |
| 5,217,459 A | 6/1993 | Kamerling | 606/48 |
| 5,230,334 A | 7/1993 | Klopotek | 601/3 |
| 5,261,410 A | 11/1993 | Alfano et al. | 600/475 |
| 5,267,994 A | 12/1993 | Gentelia et al. | 606/15 |
| 5,267,997 A | 12/1993 | Farin et al. | 606/38 |
| 5,273,524 A | 12/1993 | Fox et al. | 604/21 |
| 5,277,201 A | 1/1994 | Stern | 607/98 |
| 5,281,216 A | 1/1994 | Klicek | 606/42 |
| 5,290,273 A | 3/1994 | Tan | 606/9 |
| 5,290,282 A | 3/1994 | Casscells | 606/29 |
| 5,300,069 A | 4/1994 | Hunsberger et al. | 606/37 |
| 5,306,238 A | 4/1994 | Fleenor | 606/42 |
| 5,312,400 A | 5/1994 | Bales et al. | 606/41 |
| 5,314,406 A | 5/1994 | Arias et al. | 604/21 |
| 5,318,564 A | 6/1994 | Eggers | 606/47 |
| 5,324,254 A | 6/1994 | Phillips | 604/21 |
| 5,330,470 A | 7/1994 | Hagen | 606/42 |
| 5,334,140 A | 8/1994 | Philips | 604/35 |
| 5,336,443 A | 8/1994 | Odashima | 252/511 |
| 5,342,357 A | 8/1994 | Nardella | 606/40 |
| 5,366,443 A | 11/1994 | Eggers et al. | 604/114 |
| 5,370,675 A | 12/1994 | Edwards et al. | 607/101 |
| 5,374,261 A | 12/1994 | Yoon | 604/385.01 |
| 5,374,265 A | 12/1994 | Sand | 606/5 |
| 5,375,588 A | 12/1994 | Yoon | 128/4 |
| 5,380,277 A | 1/1995 | Phillips | 604/33 |
| 5,380,316 A | 1/1995 | Aita | 606/7 |
| 5,383,876 A | 1/1995 | Nardella | 606/49 |
| 5,383,917 A | 1/1995 | Desai et al. | 607/702 |
| 5,389,096 A | 2/1995 | Aita | 606/15 |
| 5,395,312 A | 3/1995 | Desai | 604/22 |
| 5,400,267 A | 3/1995 | Denen et al. | 702/59 |
| 5,401,272 A | 3/1995 | Perkins | 606/15 |
| 5,403,311 A | 4/1995 | Abele et al. | 606/49 |
| 5,417,687 A | 5/1995 | Nardella et al. | 606/32 |
| 5,419,767 A | 5/1995 | Eggers et al. | 604/114 |
| 5,423,810 A | 6/1995 | Goble et al. | 606/40 |
| 5,423,882 A | 6/1995 | Jackman et al. | 607/122 |
| 5,429,138 A | 7/1995 | Jamshidi | 600/566 |
| 5,433,739 A | 7/1995 | Sluijter et al. | 607/99 |
| 5,436,566 A | 7/1995 | Thompson et al. | 324/713 |
| 5,437,662 A | 8/1995 | Nardella | 606/40 |
| 5,438,302 A | 8/1995 | Goble | 331/167 |
| 5,439,446 A | 8/1995 | Barry | 604/103 |
| 5,441,499 A | 8/1995 | Fritzsch | 606/45 |
| 5,451,224 A | 9/1995 | Goble et al. | 606/48 |
| 5,454,809 A | 10/1995 | Janssen | 606/41 |
| 5,458,596 A | 10/1995 | Lax et al. | 606/31 |
| 5,496,312 A | 3/1996 | Klicek | 606/34 |
| 5,496,314 A | 3/1996 | Eggers | 606/41 |
| 5,496,317 A | 3/1996 | Goble et al. | 606/48 |
| 5,514,130 A | 5/1996 | Baker | 606/41 |
| 5,542,945 A | 8/1996 | Fritzsch | 606/48 |
| 5,554,152 A | 9/1996 | Aita | 606/7 |
| 5,556,397 A | 9/1996 | Long et al. | 606/48 |

(56) References Cited

U.S. PATENT DOCUMENTS

| | | | |
|---|---|---|---|
| 5,562,703 A | 10/1996 | Desai | 606/210 |
| 5,569,242 A | 10/1996 | Lax et al. | 606/42 |
| 5,571,100 A | 11/1996 | Goble et al. | 606/41 |
| 5,571,189 A | 11/1996 | Kuslich | 623/17.12 |
| 5,584,872 A | 12/1996 | LaFontaine et al. | 607/117 |
| 5,609,151 A | 3/1997 | Mulier et al. | 128/642 |
| 5,617,854 A | 4/1997 | Munsif | 600/374 |
| 5,618,587 A | 4/1997 | Markle et al. | 427/430.1 |
| 5,626,136 A | 5/1997 | Webster, Jr. | 600/373 |
| 5,626,576 A | 5/1997 | Janssen | 606/41 |
| 5,632,761 A | 5/1997 | Smith et al. | 606/192 |
| 5,633,578 A | 5/1997 | Eggers et al. | 323/301 |
| 5,647,869 A | 7/1997 | Goble et al. | 606/37 |
| 5,660,836 A | 8/1997 | Knowlton | 424/400 |
| 5,662,680 A | 9/1997 | Desai | 606/210 |
| 5,676,693 A | 10/1997 | LaFontaine et al. | 607/116 |
| 5,681,282 A | 10/1997 | Eggers et al. | 604/114 |
| 5,683,366 A | 11/1997 | Eggers et al. | 604/114 |
| 5,697,281 A | 12/1997 | Eggers et al. | 604/114 |
| 5,697,536 A | 12/1997 | Eggers et al. | 604/114 |
| 5,697,882 A | 12/1997 | Eggers et al. | 604/114 |
| 5,697,909 A | 12/1997 | Eggers et al. | 604/114 |
| 5,700,262 A | 12/1997 | Acosta et al. | 606/48 |
| 5,720,744 A | 2/1998 | Eggleston et al. | 606/40 |
| 5,725,524 A | 3/1998 | Mulier et al. | 606/41 |
| 5,762,629 A | 6/1998 | Kambin | 604/164.11 |
| 5,766,153 A | 6/1998 | Eggers et al. | 604/114 |
| 5,766,252 A | 6/1998 | Henry et al. | 623/17.16 |
| 5,785,705 A | 7/1998 | Baker | 606/32 |
| 5,807,306 A | 9/1998 | Shapland et al. | 604/21 |
| 5,807,395 A | 9/1998 | Mulier et al. | 606/41 |
| 5,810,764 A | 9/1998 | Eggers et al. | 604/23 |
| 5,810,809 A | 9/1998 | Rydell | 606/49 |
| 5,817,033 A | 10/1998 | Desantis et al. | 600/562 |
| 5,820,580 A | 10/1998 | Edwards et al. | 604/22 |
| 5,823,955 A | 10/1998 | Kuck et al. | 600/374 |
| 5,836,875 A | 11/1998 | Webster, Jr. | 600/374 |
| 5,843,019 A | 12/1998 | Eggers et al. | 604/22 |
| 5,846,196 A | 12/1998 | Siekmeyer et al. | 600/374 |
| 5,849,009 A | 12/1998 | Bernaz | 606/36 |
| 5,860,951 A | 1/1999 | Eggers | 604/510 |
| 5,860,974 A | 1/1999 | Abele | 606/41 |
| 5,860,975 A | 1/1999 | Goble et al. | 606/45 |
| 5,871,469 A | 2/1999 | Eggers et al. | 604/114 |
| 5,871,470 A | 2/1999 | McWha | 604/158 |
| 5,873,855 A | 2/1999 | Eggers et al. | 604/114 |
| 5,877,289 A | 3/1999 | Thorpe et al. | 530/387.7 |
| 5,885,277 A | 3/1999 | Korth | 606/35 |
| 5,888,198 A | 3/1999 | Eggers et al. | 604/114 |
| 5,891,095 A | 4/1999 | Eggers et al. | 604/114 |
| 5,891,134 A | 4/1999 | Goble et al. | 606/27 |
| 5,897,553 A | 4/1999 | Mulier | 606/41 |
| 5,902,272 A | 5/1999 | Eggers et al. | 604/114 |
| 5,916,214 A | 6/1999 | Cosio et al. | 606/41 |
| 5,925,042 A | 7/1999 | Gough et al. | 606/41 |
| 5,935,083 A | 8/1999 | Williams | 600/561 |
| 5,941,869 A | 8/1999 | Patterson et al. | 604/508 |
| 5,944,715 A | 8/1999 | Goble et al. | 606/41 |
| 5,954,716 A | 9/1999 | Sharkey et al. | 606/32 |
| 5,980,504 A | 11/1999 | Sharkey et al. | 604/510 |
| 6,004,319 A | 12/1999 | Goble et al. | 606/48 |
| 6,007,570 A | 12/1999 | Sharkey et al. | 607/96 |
| 6,013,076 A | 1/2000 | Goble et al. | 606/41 |
| 6,014,584 A | 1/2000 | Hofmann et al. | 604/21 |
| 6,015,406 A | 1/2000 | Goble et al. | 606/41 |
| 6,024,733 A | 2/2000 | Eggers et al. | 604/500 |
| 6,027,501 A | 2/2000 | Goble et al. | 606/41 |
| 6,036,681 A | 3/2000 | Hooven | 604/506 |
| 6,039,734 A | 3/2000 | Goble et al. | 606/41 |
| 6,045,532 A | 4/2000 | Eggers et al. | 604/114 |
| 6,047,700 A | 4/2000 | Eggers et al. | 128/898 |
| 6,053,172 A | 4/2000 | Hovda et al. | 128/898 |
| 6,056,746 A | 5/2000 | Goble et al. | 606/48 |
| 6,063,079 A | 5/2000 | Hovda et al. | 606/41 |
| 6,066,134 A | 5/2000 | Eggers et al. | 606/32 |
| 6,068,628 A | 5/2000 | Fanton et al. | 606/41 |
| 6,073,051 A | 6/2000 | Sharkey et al. | 607/99 |
| 6,074,386 A | 6/2000 | Goble et al. | 606/34 |
| 6,086,584 A | 7/2000 | Miller | 606/41 |
| 6,090,106 A | 7/2000 | Goble et al. | 606/41 |
| 6,093,186 A | 7/2000 | Goble et al. | 606/34 |
| 6,093,187 A | 7/2000 | Lecuyer | 606/45 |
| 6,095,149 A | 8/2000 | Sharkey et al. | 128/898 |
| 6,096,036 A | 8/2000 | Bowe et al. | 606/41 |
| 6,102,046 A | 8/2000 | Weinstein et al. | 128/898 |
| 6,105,581 A | 8/2000 | Eggers et al. | 128/898 |
| 6,109,268 A | 8/2000 | Thapliyal et al. | 128/898 |
| 6,117,109 A | 9/2000 | Eggers et al. | 604/114 |
| 6,122,549 A | 9/2000 | Sharkey et al. | 607/99 |
| 6,126,682 A | 10/2000 | Sharkey et al. | 607/96 |
| 6,142,992 A | 11/2000 | Cheng et al. | 606/34 |
| 6,146,380 A | 11/2000 | Racz et al. | 606/41 |
| 6,149,620 A | 11/2000 | Baker et al. | 604/22 |
| 6,159,194 A | 12/2000 | Eggers et al. | 604/500 |
| 6,159,208 A | 12/2000 | Hovda et al. | 606/41 |
| 6,168,593 B1 | 1/2001 | Sharkey et al. | 606/34 |
| 6,174,309 B1 | 1/2001 | Wrublewski et al. | 606/45 |
| 6,176,857 B1 | 1/2001 | Ashley | 606/32 |
| 6,179,824 B1 | 1/2001 | Eggers et al. | 604/500 |
| 6,179,836 B1 | 1/2001 | Eggers et al. | 606/45 |
| 6,183,469 B1 | 2/2001 | Thapliyal et al. | 606/41 |
| 6,187,048 B1 | 2/2001 | Milner et al. | 623/17.12 |
| 6,190,381 B1 | 2/2001 | Olsen et al. | 606/32 |
| 6,203,542 B1 | 3/2001 | Ellsberry et al. | 606/41 |
| 6,210,402 B1 | 4/2001 | Olsen et al. | 606/32 |
| 6,214,001 B1 | 4/2001 | Casscells et al. | 606/41 |
| 6,224,592 B1 | 5/2001 | Eggers et al. | 606/32 |
| 6,228,078 B1 | 5/2001 | Eggers | 606/32 |
| 6,228,081 B1 | 5/2001 | Goble | 606/34 |
| 6,235,020 B1 | 5/2001 | Cheng et al. | 606/34 |
| 6,237,604 B1 | 5/2001 | Burnside et al. | 128/897 |
| 6,238,391 B1 | 5/2001 | Olsen et al. | 606/41 |
| 6,245,107 B1 | 6/2001 | Ferree | 606/61 |
| 6,254,600 B1 | 7/2001 | Willink et al. | 606/41 |
| 6,258,086 B1 | 7/2001 | Ashley et al. | 606/41 |
| 6,261,286 B1 | 7/2001 | Goble et al. | 606/34 |
| 6,261,311 B1 | 7/2001 | Sharkey et al. | 607/96 |
| 6,264,650 B1 | 7/2001 | Hovda et al. | 606/32 |
| 6,264,651 B1 | 7/2001 | Underwood et al. | 606/32 |
| 6,264,652 B1 | 7/2001 | Eggers et al. | 606/41 |
| 6,270,460 B1 | 8/2001 | McCartan et al. | 600/459 |
| 6,273,861 B1 | 8/2001 | Bates et al. | 600/567 |
| 6,277,112 B1 | 8/2001 | Underwood et al. | 606/32 |
| 6,280,441 B1 | 8/2001 | Ryan | 606/45 |
| 6,283,961 B1 | 9/2001 | Underwood et al. | 606/41 |
| 6,293,942 B1 | 9/2001 | Goble et al. | 606/38 |
| 6,296,636 B1 | 10/2001 | Cheng et al. | 606/32 |
| 6,296,638 B1 | 10/2001 | Davison et al. | 606/41 |
| 6,306,134 B1 | 10/2001 | Goble et al. | 606/42 |
| 6,308,089 B1 | 10/2001 | von der Ruhr et al. | 600/338 |
| 6,309,387 B1 | 10/2001 | Eggers et al. | 606/41 |
| 6,312,408 B1 | 11/2001 | Eggers et al. | 604/114 |
| 6,319,250 B1 | 11/2001 | Falwell et al. | 606/41 |
| 6,322,549 B1 | 11/2001 | Eggers et al. | 604/500 |
| 6,330,478 B1 | 12/2001 | Lee et al. | 607/101 |
| 6,355,032 B1 | 3/2002 | Hovda et al. | 606/32 |
| 6,363,937 B1 | 4/2002 | Hovda et al. | 128/898 |
| 6,364,877 B1 | 4/2002 | Goble et al. | 606/34 |
| 6,379,350 B1 | 4/2002 | Sharkey et al. | 606/41 |
| 6,379,351 B1 | 4/2002 | Thapliyal et al. | 606/41 |
| 6,391,025 B1 | 5/2002 | Weinstein et al. | 606/41 |
| 6,402,740 B1 | 6/2002 | Ellis et al. | 606/28 |
| 6,416,507 B1 | 7/2002 | Eggers et al. | 606/32 |
| 6,416,508 B1 | 7/2002 | Eggers et al. | 606/32 |
| 6,416,509 B1 | 7/2002 | Goble et al. | 606/37 |
| 6,428,576 B1 | 8/2002 | Haldimann | 623/17.16 |
| 6,432,103 B1 | 8/2002 | Ellsberry et al. | 606/41 |
| 6,443,988 B2 | 9/2002 | Felt et al. | 623/17.12 |
| 6,461,357 B1 | 10/2002 | Sharkey et al. | 606/45 |
| 6,464,695 B2 | 10/2002 | Hovda et al. | 606/32 |
| 6,468,270 B1 | 10/2002 | Hovda et al. | 606/32 |
| 6,468,274 B1 | 10/2002 | Alleyne et al. | 606/32 |
| 6,468,275 B1 | 10/2002 | Wampler et al. | 606/48 |
| 6,482,201 B1 | 11/2002 | Olsen et al. | 606/41 |

(56) References Cited

U.S. PATENT DOCUMENTS

| | | | |
|---|---|---|---|
| 6,497,704 B2 | 12/2002 | Ein-Gal | 606/41 |
| 6,500,173 B2 | 12/2002 | Underwood et al. | 606/32 |
| 6,508,839 B1 | 1/2003 | Lambrecht et al. | 623/17.16 |
| 6,517,498 B1 | 2/2003 | Burbank et al. | 600/564 |
| 6,530,922 B2 | 3/2003 | Cosman | 606/34 |
| 6,540,741 B1 | 4/2003 | Underwood et al. | 606/32 |
| 6,558,390 B2 | 5/2003 | Cragg | 606/80 |
| 6,562,033 B2 | 5/2003 | Shah et al. | 606/41 |
| 6,575,968 B1 | 6/2003 | Eggers et al. | 606/41 |
| 6,578,579 B2 | 6/2003 | Burnside | 128/897 |
| 6,589,237 B2 | 7/2003 | Woloszko et al. | 606/41 |
| 6,602,248 B1 | 8/2003 | Sharps et al. | 606/32 |
| 6,604,003 B2 | 8/2003 | Fredricks et al. | 607/99 |
| 6,611,793 B1 | 8/2003 | Burnside et al. | 2/183 |
| 6,620,155 B2 | 9/2003 | Underwood et al. | 606/32 |
| 6,620,156 B1 | 9/2003 | Garito et al. | 606/50 |
| 6,622,731 B2 | 9/2003 | Daniel et al. | 128/898 |
| 6,632,193 B1 | 10/2003 | Davison et al. | 604/22 |
| 6,632,220 B1 | 10/2003 | Eggers et al. | 606/41 |
| 6,635,034 B1 | 10/2003 | Cosmescu | 604/289 |
| 6,635,087 B2 | 10/2003 | Angelucci et al. | 623/17.11 |
| 6,645,247 B2 | 11/2003 | Ferree | 623/17.11 |
| 6,679,886 B2 | 1/2004 | Weikel et al. | 606/79 |
| 6,699,244 B2 | 3/2004 | Carranza et al. | 606/41 |
| 6,712,811 B2 | 3/2004 | Underwood et al. | 606/32 |
| 6,726,684 B1 | 4/2004 | Woloszko et al. | 606/32 |
| 6,740,093 B2 | 5/2004 | Hochschuler et al. | 606/94 |
| 6,746,451 B2 | 6/2004 | Middleton et al. | 606/79 |
| 6,749,604 B1 | 6/2004 | Eggers et al. | 606/41 |
| 6,749,605 B2 | 6/2004 | Ashley et al. | 606/41 |
| 6,749,608 B2 | 6/2004 | Garito et al. | 606/45 |
| 6,758,846 B2 | 7/2004 | Goble et al. | 606/41 |
| 6,761,718 B2 | 7/2004 | Madsen | 606/50 |
| 6,770,071 B2 | 8/2004 | Woloszko et al. | 606/41 |
| 6,772,012 B2 | 8/2004 | Woloszko et al. | 607/99 |
| 6,780,178 B2 | 8/2004 | Palanker et al. | 600/411 |
| 6,780,180 B1 | 8/2004 | Goble et al. | 606/41 |
| 6,802,842 B2 | 10/2004 | Ellman et al. | 606/45 |
| 6,827,716 B2 | 12/2004 | Ryan et al. | 606/41 |
| 6,837,884 B2 | 1/2005 | Woloszko | 606/32 |
| 6,837,887 B2 | 1/2005 | Woloszko et al. | 606/41 |
| 6,837,888 B2 | 1/2005 | Ciarrocca et al. | 606/41 |
| 6,878,155 B2 | 4/2005 | Sharkey et al. | 607/96 |
| 6,918,908 B2 | 7/2005 | Bonner et al. | 606/41 |
| 6,920,883 B2 | 7/2005 | Bessette et al. | 128/898 |
| 6,921,399 B2 | 7/2005 | Carmel et al. | 606/41 |
| 6,929,640 B1 | 8/2005 | Underwood et al. | 606/32 |
| 6,949,096 B2 | 9/2005 | Davison et al. | 606/41 |
| 6,960,204 B2 | 11/2005 | Eggers et al. | 606/32 |
| 6,974,453 B2 | 12/2005 | Woloszko et al. | 606/41 |
| 6,974,480 B2 | 12/2005 | Messerli et al. | 623/17.11 |
| 6,984,231 B2 | 1/2006 | Goble et al. | 606/37 |
| 6,991,631 B2 | 1/2006 | Woloszko et al. | 606/41 |
| 6,997,885 B2 | 2/2006 | Lubock et al. | 600/567 |
| 6,997,925 B2 | 2/2006 | Maguire et al. | 606/41 |
| 7,001,431 B2 | 2/2006 | Bao et al. | 623/17.12 |
| 7,004,941 B2 | 2/2006 | Tvinnereim et al. | 606/41 |
| 7,014,633 B2 | 3/2006 | Cragg | 604/500 |
| 7,041,102 B2 | 5/2006 | Truckai et al. | 606/51 |
| 7,070,596 B1 | 7/2006 | Woloszko et al. | 606/41 |
| 7,090,672 B2 | 8/2006 | Underwood et al. | 606/41 |
| 7,094,215 B2 | 8/2006 | Davison et al. | 604/22 |
| 7,104,986 B2 | 9/2006 | Hovda et al. | 606/32 |
| 7,104,989 B2 | 9/2006 | Skarda | 606/41 |
| 7,108,696 B2 | 9/2006 | Daniel et al. | 606/41 |
| 7,131,969 B1 | 11/2006 | Hovda et al. | 606/45 |
| 7,169,143 B2 | 1/2007 | Eggers et al. | 606/32 |
| 7,172,591 B2 | 2/2007 | Harano et al. | 606/41 |
| 7,179,225 B2 | 2/2007 | Shluzas et al. | 600/219 |
| 7,179,255 B2 | 2/2007 | Lettice et al. | 606/32 |
| 7,186,234 B2 | 3/2007 | Dahla et al. | 604/22 |
| 7,192,428 B2 | 3/2007 | Eggers et al. | 606/41 |
| 7,201,750 B1 | 4/2007 | Eggers et al. | 606/41 |
| 7,217,268 B2 | 5/2007 | Eggers et al. | 606/32 |
| 7,241,293 B2 | 7/2007 | Davison | 600/410 |
| 7,241,294 B2 | 7/2007 | Reschke | 606/41 |
| 7,270,658 B2 | 9/2007 | Woloszko et al. | 606/32 |
| 7,270,659 B2 | 9/2007 | Hovda et al. | 606/32 |
| 7,270,661 B2 | 9/2007 | Dahla et al. | 606/41 |
| 7,276,063 B2 | 10/2007 | Davison et al. | 606/45 |
| 7,278,972 B2 | 10/2007 | Lamoureux et al. | 600/567 |
| 7,297,143 B2 | 11/2007 | Woloszko et al. | 606/41 |
| 7,297,145 B2 | 11/2007 | Woloszko et al. | 606/41 |
| 7,318,823 B2 | 1/2008 | Sharps et al. | 606/32 |
| 7,331,956 B2 | 2/2008 | Hovda et al. | 606/32 |
| RE40,156 E | 3/2008 | Sharps et al. | 606/32 |
| 7,357,798 B2 | 4/2008 | Sharps et al. | 606/32 |
| 7,387,625 B2 | 6/2008 | Hovda et al. | 606/32 |
| 7,393,351 B2 | 7/2008 | Woloszko et al. | 606/32 |
| 7,419,488 B2 | 9/2008 | Ciarrocca et al. | 606/41 |
| 7,429,260 B2 | 9/2008 | Underwood et al. | 606/32 |
| 7,429,262 B2 | 9/2008 | Woloszko et al. | 606/46 |
| 7,435,247 B2 | 10/2008 | Woloszko et al. | 604/45 |
| 7,442,191 B2 | 10/2008 | Hovda et al. | 606/41 |
| 7,445,618 B2 | 11/2008 | Eggers et al. | 604/48 |
| 7,449,021 B2 | 11/2008 | Underwood et al. | 606/32 |
| 7,462,178 B2 | 12/2008 | Woloszko et al. | 607/105 |
| 7,468,059 B2 | 12/2008 | Eggers et al. | 606/32 |
| 7,491,200 B2 | 2/2009 | Underwood et al. | 606/32 |
| 7,507,236 B2 | 3/2009 | Eggers et al. | 606/41 |
| 7,572,251 B1 | 8/2009 | Davison et al. | 604/500 |
| 7,628,780 B2 | 12/2009 | Bonner et al. | 604/500 |
| 7,632,267 B2 | 12/2009 | Dahla | 606/41 |
| 7,682,368 B1 | 3/2010 | Bombard et al. | 606/142 |
| 7,691,101 B2 | 4/2010 | Davison et al. | 606/41 |
| 7,704,249 B2 | 4/2010 | Woloszko et al. | 606/48 |
| 7,708,733 B2 | 5/2010 | Sanders et al. | 606/41 |
| 7,883,515 B2 | 2/2011 | Kear | 606/127 |
| 7,951,141 B2 | 5/2011 | Sharps et al. | 606/32 |
| 7,976,554 B2 | 7/2011 | Newell et al. | 606/144 |
| 8,292,887 B2 | 10/2012 | Woloszko et al. | 606/48 |
| 2002/0029036 A1 | 3/2002 | Goble et al. | 606/38 |
| 2002/0049438 A1 | 4/2002 | Sharkey et al. | 606/41 |
| 2002/0082698 A1 | 6/2002 | Parenteau et al. | 623/17.16 |
| 2002/0120337 A1 | 8/2002 | Cauthen | 623/17.16 |
| 2003/0013986 A1 | 1/2003 | Saadat | 600/549 |
| 2003/0088245 A1 | 5/2003 | Woloszko et al. | 606/41 |
| 2003/0130655 A1 | 7/2003 | Woloszko et al. | 606/45 |
| 2003/0130738 A1 | 7/2003 | Hovda et al. | 623/17.11 |
| 2003/0158545 A1 | 8/2003 | Hovda et al. | 606/32 |
| 2003/0171743 A1 | 9/2003 | Tasto et al. | 606/32 |
| 2003/0208196 A1 | 11/2003 | Stone | 606/41 |
| 2003/0212396 A1 | 11/2003 | Eggers et al. | 606/41 |
| 2004/0087937 A1 | 5/2004 | Eggers et al. | 606/41 |
| 2004/0116922 A1 | 6/2004 | Hovda et al. | 606/41 |
| 2004/0127893 A1 | 7/2004 | Hovda | 606/41 |
| 2004/0230190 A1 | 11/2004 | Dahla et al. | 604/41 |
| 2005/0004634 A1 | 1/2005 | Ricart et al. | 606/41 |
| 2005/0043682 A1 | 2/2005 | Kucklick et al. | 604/164.09 |
| 2005/0059862 A1 | 3/2005 | Phan | 600/176 |
| 2005/0096645 A1 | 5/2005 | Wellman et al. | 606/41 |
| 2005/0261754 A1 | 11/2005 | Woloszko et al. | 606/32 |
| 2005/0267553 A1 | 12/2005 | Staunton et al. | 607/101 |
| 2005/0288665 A1 | 12/2005 | Woloszko et al. | 606/41 |
| 2006/0036237 A1 | 2/2006 | Davison et al. | 606/41 |
| 2006/0095031 A1 | 5/2006 | Ormsby | 606/34 |
| 2006/0178670 A1 | 8/2006 | Woloszko et al. | 606/48 |
| 2006/0189971 A1 | 8/2006 | Tasto et al. | 606/32 |
| 2006/0253117 A1 | 11/2006 | Hovda et al. | 128/898 |
| 2006/0259025 A1 | 11/2006 | Dahla | 607/108 |
| 2007/0106288 A1 | 5/2007 | Woloszko et al. | 606/41 |
| 2007/0149966 A1 | 6/2007 | Dahla et al. | 606/41 |
| 2007/0161981 A1 | 7/2007 | Sanders et al. | 606/41 |
| 2007/0208334 A1 | 9/2007 | Woloszko et al. | 606/41 |
| 2007/0208335 A1 | 9/2007 | Woloszko et al. | 606/41 |
| 2007/0282323 A1 | 12/2007 | Woloszko et al. | 606/41 |
| 2008/0015565 A1* | 1/2008 | Davison | 606/37 |
| 2008/0243117 A1 | 10/2008 | Sharps et al. | 606/41 |
| 2009/0105543 A1 | 4/2009 | Miller et al. | 600/155 |
| 2009/0125011 A1* | 5/2009 | Behzadian | 606/33 |
| 2009/0299220 A1 | 12/2009 | Field et al. | 600/567 |
| 2010/0114110 A1 | 5/2010 | Taft et al. | 600/184 |

(56) References Cited

U.S. PATENT DOCUMENTS

| | | | | |
|---|---|---|---|---|
| 2010/0204693 A1 | 8/2010 | Sanders et al. | ............... | 606/41 |
| 2011/0112373 A1 | 5/2011 | Ainsworth et al. | ............ | 600/207 |
| 2011/0288619 A1 | 11/2011 | Pianca | ..................... | 607/116 |

FOREIGN PATENT DOCUMENTS

| | | | | |
|---|---|---|---|---|
| DE | 3930451 A1 | 3/1991 | ............ | A61B 17/39 |
| DE | 9490466 | 7/1996 | ............ | A61B 17/38 |
| EP | 515 867 | 12/1992 | ............ | A61B 17/36 |
| EP | 0703461 A2 | 3/1996 | ............ | G01B 27/02 |
| EP | 0740926 A2 | 11/1996 | ............ | A61B 17/39 |
| EP | 0754437 A2 | 1/1997 | ............ | A61B 17/39 |
| EP | 719162 B1 | 11/1997 | ............ | A61N 1/05 |
| EP | 774926 B1 | 6/1999 | ............ | A61B 17/39 |
| EP | 0694290 B1 | 11/2000 | ............ | A61B 18/04 |
| EP | 886495 B1 | 2/2003 | ............ | A61B 18/08 |
| FR | 2313949 | 1/1977 | ............ | A61N 3/02 |
| GB | 2 308 979 | 7/1997 | ............ | A61B 17/36 |
| GB | 2 308 980 | 7/1997 | ............ | A61B 17/36 |
| GB | 2 308 981 | 7/1997 | ............ | A61B 17/36 |
| GB | 2 327 350 | 1/1999 | ............ | A61B 17/39 |
| GB | 2 327 351 | 1/1999 | ............ | A61B 17/39 |
| GB | 2 327 352 | 1/1999 | ............ | A61B 17/39 |
| JP | 57-57802 | 4/1982 | ............ | A61B 1/00 |
| JP | 57-117843 | 7/1982 | ............ | A61B 17/39 |
| JP | 10/504732 | 5/1998 | ............ | A61B 17/56 |
| WO | 90/03152 | 4/1990 | ............ | A61B 17/39 |
| WO | 90/07303 | 7/1990 | ............ | A61B 17/39 |
| WO | 92/21278 | 12/1992 | ............ | A61B 5/04 |
| WO | 93/13816 | 7/1993 | ............ | A61B 17/36 |
| WO | 93/20747 | 10/1993 | ............ | A61B 5/00 |
| WO | 94/04220 | 3/1994 | | |
| WO | 94/08524 | 4/1994 | ............ | A61B 17/32 |
| WO | 94/08654 | 4/1994 | ............ | A61M 37/00 |
| WO | 94/14383 | 7/1994 | ............ | A61B 17/36 |
| WO | 94/26228 | 11/1994 | ............ | A61B 17/00 |
| WO | 95/05781 | 3/1995 | ............ | A61B 17/00 |
| WO | 95/05867 | 3/1995 | ............ | A61B 17/00 |
| WO | 95/09576 | 4/1995 | ............ | A61B 17/39 |
| WO | 95/30373 | 11/1995 | ............ | A61B 17/00 |
| WO | 95/34259 | 12/1995 | ............ | A61F 5/48 |
| WO | 96/00042 | 1/1996 | ............ | A61B 17/39 |
| WO | 96/07360 | 3/1996 | ............ | A61B 17/00 |
| WO | 96/20652 | 7/1996 | ............ | A61B 18/14 |
| WO | 96/23449 | 8/1996 | ............ | A61B 17/00 |
| WO | 96/39914 | 12/1996 | ............ | A61B 1/00 |
| WO | 96/41574 | 12/1996 | ............ | A61B 17/00 |
| WO | 97/00070 | 1/1997 | ............ | A61K 31/415 |
| WO | 97/00646 | 1/1997 | ............ | A61B 17/39 |
| WO | 97/00647 | 1/1997 | ............ | A61B 17/39 |
| WO | 97/23169 | 7/1997 | ............ | A61B 17/39 |
| WO | 97/24073 | 7/1997 | ............ | A61B 17/39 |
| WO | 97/24074 | 7/1997 | ............ | A61B 17/39 |
| WO | 97/24992 | 7/1997 | ............ | A61B 18/12 |
| WO | 97/24993 | 7/1997 | ............ | A61B 17/39 |
| WO | 97/24994 | 7/1997 | ............ | A61B 17/39 |
| WO | 97/48345 | 12/1997 | ............ | A61B 17/39 |
| WO | 97/48346 | 12/1997 | ............ | A61B 17/39 |
| WO | 98/00070 | 1/1998 | ............ | A61B 18/14 |
| WO | 98/01087 | 1/1998 | ............ | A61F 1/03 |
| WO | 98/03117 | 1/1998 | ............ | A61B 17/00 |
| WO | 98/03220 | 1/1998 | ............ | A61B 18/14 |
| WO | 98/07468 | 2/1998 | ............ | A61N 1/40 |
| WO | 98/11944 | 3/1998 | ............ | A61N 5/02 |
| WO | 98/14131 | 4/1998 | ............ | A61B 18/00 |
| WO | 98/17190 | 4/1998 | ............ | A61B 18/00 |
| WO | 98/27879 | 7/1998 | ............ | A61B 17/36 |
| WO | 98/27880 | 7/1998 | ............ | A61B 17/39 |
| WO | 99/03414 | 1/1999 | ............ | A61B 18/14 |
| WO | 99/20185 | 4/1999 | ............ | A61B 17/20 |
| WO | 99/42037 | 8/1999 | ............ | A61B 18/14 |
| WO | 99/47058 | 9/1999 | ............ | A61B 17/39 |
| WO | 99/51155 | 10/1999 | ............ | A61B 17/36 |
| WO | 99/51158 | 10/1999 | ............ | A61B 17/39 |
| WO | 00/01313 | 1/2000 | ............ | A61B 17/39 |
| WO | 00/07507 | 2/2000 | | |
| WO | 00/10475 | 3/2000 | ............ | A61B 18/14 |
| WO | 00/62698 | 10/2000 | ............ | A61B 18/14 |
| WO | 00/71043 | 11/2000 | ............ | A61B 18/14 |
| WO | 01/26570 | 4/2001 | ............ | A61B 18/14 |
| WO | 01/87154 | 5/2001 | ............ | A61B 5/05 |
| WO | 01/82813 | 11/2001 | ............ | A61B 18/14 |
| WO | 02/11635 | 2/2002 | ............ | A61B 18/14 |
| WO | 02/36028 | 5/2002 | ............ | A61B 18/12 |
| WO | 03/024506 | 3/2003 | ............ | A61B 18/14 |
| WO | 03/089997 A2 | 10/2003 | | |
| WO | 2004/022155 | 3/2004 | ............ | A61B 18/18 |
| WO | 2005/039390 | 5/2005 | ............ | A61B 18/18 |
| WO | 2005/122938 | 12/2005 | ............ | A61B 18/18 |
| WO | 2005/125287 | 12/2005 | ............ | A61B 18/00 |

OTHER PUBLICATIONS

BiLAP Generator Settings, Jun. 1991.
BiLAP IFU 910026-001 Rev A for BiLAP Model 3525, J-Hook, 4 pgs, May 20, 1991.
BiLAP IFU 910033-002 Rev A for BiLAP Model 3527, L-Hook; BiLAP Model 3525, J-Hook; BiLAP Model 3529, High Angle, 2 pgs, Nov. 30, 1993.
Codman & Shurtleff, Inc. "The Malis Bipolar Coagulating and Bipolar Cutting System CMC-II" brochure, early, 2 pgs, 1991.
Codman & Shurtleff, Inc. "The Malis Bipolar Electrosurgical System CMC-III Instruction Manual" , 15 pgs, Jul. 1991.
Cook et al., "Therapeutic Medical Devices: Application and Design", Prentice Hall, Inc., 3pgs, 1982.
Dennis et al. "Evolution of Electrofulguration in Control of Bleeding of Experimental Gastric Ulcers," Digestive Diseases and Sciences, vol. 24, No. 11, 845-848, Nov. 1979.
Dobbie, A.K., "The Electrical Aspects of Surgical Diathermy, Bio Medical Engineering" *Bio-Medical Engineering* vol. 4, pp. 206-216, May 1969.
Elsasser, V.E. et al., "An Instrument for Transurethral Resection without Leakage of Current" *Acta Medicotechnica* vol. 24, No. 4, pp. 129-134, 1976.
Geddes, "Medical Device Accidents: With Illustrative Cases" CRC Press, 3 pgs, 1998.
Honig, W., "The Mechanism of Cutting in Electrosurgery" *IEEE* pp. 58-65, 1975.
Kramolowsky et al. "The Urological App of Electorsurgery" *J. of Urology* vol. 146, pp. 669-674, 1991.
Kramolowsky et al. "Use of 5F Bipolar Electrosurgical Probe in Endoscopic Urological Procedures" *J. of Urology* vol. 143, pp. 275-277, 1990.
Lee, B et al. "Thermal Compression and Molding of Artherosclerotic Vascular Tissue with Use" JACC vol. 13(5), pp. 1167-1171, 1989.
Letter from Department of Health to Jerry Malis dated Jan. 24, 1991, 3 pgs.
Letter from Department of Health to Jerry Malis dated Jul. 25, 1985, 1 pg.
Letter from Jerry Malis to FDA dated Jul. 25, 1985, 2 pgs.
Lu, et al., "Electrical Thermal Angioplasty: Catheter Design Features, In Vitro Tissue Ablation Studies and in Vitro Experimental Findings," *Am J. Cardiol* vol. 60, pp. 1117-1122, Nov. 1, 1987.
Malis, L., "Electrosurgery, Technical Note," *J. Neursurg.*, vol. 85, pp. 970-975, Nov. 1996.
Malis, L., "Excerpted from a seminar by Leonard I. Malis, M.D. at the 1995 American Association of Neurological Surgeons Meeting," 1pg, 1995.
Malis, L., "Instrumentation for Microvascular Neurosurgery" *Cerebrovascular Surgery*, vol. 1, pp. 245-260, 1985.
Malis, L., "New Trends in Microsurgery and Applied Technology," *Advanced Technology in Neurosurgery*, pp. 1-16, 1988.
Malis, L., "The Value of Irrigation During Bipolar Coagulation" See ARTC 21602, 1 pg, Apr. 9, 1993.
Nardella, P.C., *SPIE* 1068: pp. 42-49, Radio Frequency Energy and Impedance Feedback, 1989.
O'Malley, Schaum's Outline of Theory and Problems of Basic Circuit Analysis, McGraw-Hill, $2^{nd}$ Ed., pp. 3-5, 1992.

(56) References Cited

OTHER PUBLICATIONS

Olsen MD, Bipolar Laparoscopic Cholecstectomy Lecture (marked confidential), 12 pgs, Oct. 7, 1991.
Pearce, John A. "Electrosurgery", pp. 17, 69-75, 87, John Wiley & Sons, New York, 1986.
Pearce, John A., "Electrosurgery", Handbook of Biomedical Engineering, chapter 3, Academic Press Inc., N.Y., pp. 98-113, 1988.
Piercey et al., "Electrosurgical Treatment of Experimental Bleeding Canine Gastric Ulcers" *Gastroenterology* vol. 74(3), pp. 527-534, 1978.
Protell et al., "Computer-Assisted Electrocoagulation: Bipolar v. Monopolar in the Treatment of Experimental Canine Gastric Ulcer Bleeding," *Gastroenterology* vol. 80, No. 3, pp. 451-455, 1981.
Ramsey et al., "A Comparison of Bipolar and Monopolar Diathermy Probes in Experimental Animals", *Urological Research* vol. 13, pp. 99-102, 1985.
Selikowitz et al., "Electric Current and Voltage Recordings on the Myocardium During Electrosurgical Procedures in Canines," *Surgery, Gynecology & Obstetrics*, vol. 164, pp. 219-224, Mar. 1987.
Shuman, "Bipolar Versus Monopolar Electrosurgery: Clinical Applications," *Dentistry Today*, vol. 20, No. 12, 7 pgs, Dec. 2001.
Slager et al. "Spark Erosion of Arteriosclerotic Plaques" *Z. Kardiol.* 76:Suppl. 6, pp. 67-71, 1987.
Slager et al. "Vaporization of Atherosclerotice Plaques by Spark Erosion" *JACC* 5(6): pp. 1382-1386, Jun. 1985.
Stoffels, E. et al., "Investigation on the Interaction Plasma-Bone Tissue", E-MRS Spring Meeting, 1 pg, Jun. 18-21, 2002.
Stoffels, E. et al., "Biomedical Applications of Plasmas", Tutorial presented prior to the 55$^{th}$ Gaseous Electronics Conference in Minneapolis, MN, 41 pgs, Oct. 14, 2002.
Stoffels, E. et al., "Plasma Interactions with Living Cells", Eindhoven University of Technology, 1 pg, 2002.
Stoffels, E. et al., "Superficial Treatment of Mammalian Cells using Plasma Needle", J. Phys. D: Appl. Phys. 26, pp. 2908-2913, Nov. 19, 2003.
Stoffels, E. et al., "Plasma Needle", Eindhoven University of Technology, 1 pg, Nov. 28, 2003.
Stoffels, E. et al., "Plasma Physicists Move into Medicine", Physicsweb, 1 pg, Nov. 2003.
Stoffels, E. et al., "Plasma Treated Tissue Engineered Skin to Study Skin Damage", Biomechanics and Tissue Engineering, Materials Technology, 1 pg, 2003.
Stoffels, E. et al., "Plasma Treatment of Dental Cavities: A Feasibility Study", IEEE Transaction on Plasma Science, vol. 32, No. 4, pp. 1540-1542, Aug. 2004.
Stoffels, E. et al., "The Effects of UV Irradiation and Gas Plasma Treatment on Living Mammalian Cells and Bacteria: A Comparative Approach", IEEE Transaction on Plasma Science, vol. 32, No. 4, pp. 1544-1550, Aug. 2004.
Stoffels, E. et al., "Electrical and Optical Characterization of the Plasma Needle", New Journal of Physics 6, pp. 1-14, Oct. 28, 2004.
Stoffels, E. et al., "Where Plasma Meets Plasma", Eindhoven University of Technology, 23 pgs, 2004.
Stoffels, E. et al., "Gas Plasma effects on Living Cells", Physica Scripta, T107, pp. 79-82, 2004.
Stoffels, E. et al., "Plasma Treatment of Mammalian Vascular Cells: A Quantitative Description", IEEE Transaction on Plasma Science, vol. 33, No. 2, pp. 771-775, Apr. 2005.
Stoffels, E. et al., "Deactivation of *Escherichia coli* by the Plasma Needle", J. Phys. D: Appl. Phys. 38, pp. 1716-1721, May 20, 2005.
Stoffels, E. et al., "Development of a Gas Plasma Catheter for Gas Plasma Surgery", XXVIIth ICPIG, Endoven University of Technology, pp. 18-22, Jul. 2005.
Stoffels, E. et al., "Development of a Smart Positioning Sensor for the Plasma Needle", Plasma Sources Sci. Technol. 15, pp. 582-589, Jun. 27, 2006.
Stoffels, E. et al., Killing of *S. mutans* Bacteria Using a Plasma Needle at Atmospheric Pressure, IEEE Transaction on Plasma Science, vol. 34, No. 4, pp. 1317-1324, Aug. 2006.

Stoffels, E. et al., "Plasma-Needle Treatment of Substrates with Respect to Wettability and Growth of *Excherichia coli* and *Streptococcus mutans*", IEEE Transaction on Plasma Science, vol. 34, No. 4, pp. 1325-1330, Aug. 2006.
Stoffels, E. et al., "Reattachment and Apoptosis after Plasma-Needle Treatment of Cultured Cells", IEEE Transaction on Plasma Science, vol. 34, No. 4, pp. 1331-1336, Aug. 2006.
Stoffels, E. et al., "UV Excimer Lamp Irradiation of Fibroblasts: The Influence on Antioxidant Homostasis", IEEE Transaction on Plasma Science, vol. 34, No. 4, pp. 1359-1364, Aug. 2006.
Stoffels, E. et al., "Plasma Needle for In Vivo Medical Treatment: Recent Developments and Perspectives", Plasma Sources Sci. Technol. 15, pp. S169-S180, Oct. 6, 2006.
Swain, C.P., et al., "Which Electrode, A Comparison of four endoscopic methods of electrocoagulation in experimental bleeding ulcers" *Gut* vol. 25, pp. 1424-1431, 1987.
Tucker, R. et al., Abstract P14-11, p. 248, "A Bipolar Electrosurgical Turp Loop", Nov. 1989.
Tucker, R. et al. "A Comparison of Urologic Application of Bipolar Versus Monopolar Five French Electrosurgical Probes" *J. of Urology* vol. 141, pp. 662-665, 1989.
Tucker, R. et al. "In vivo effect of 5 French Bipolar and Monopolar Electrosurgical Probes on the Porcine Bladder" *Urological Research* vol. 18, pp. 291-294, 1990.
Tucker, R. et al., "Demodulated Low Frequency Currents from Electrosurgical Procedures," *Surgery, Gynecology and Obstetrics*, 159:39-43, 1984.
Tucker et al. "The interaction between electrosurgical generators, endoscopic electrodes, and tissue," Gastrointestinal Endoscopy, vol. 38, No. 2, pp. 118-122, 1992.
Valley Forge Scientific Corp., "Summary of Safety and Effective Information from 510K", 2pgs, 1991.
Valley Forge's New Products, Clinica, 475, 5, Nov. 6, 1991.
Valleylab SSE2L Instruction Manual, 11 pgs, Jan. 6, 1983.
Valleylab, Inc. "Valleylab Part No. 945 100 102 A" Surgistat Service Manual, pp. 1-46, Jul. 1988.
Wattiez, Arnaud et al., "Electrosurgery in Operative Endoscopy," Electrosurgical Effects, Blackwell Science, pp. 85-93, 1995.
Wyeth, "Electrosurgical Unit" pp. 1181-1202, 2000.
Buchelt, et al. "Excimer Laser Ablation of Fibrocartilage: An In Vitro and In Vivo Study", Lasers in Surgery and Medicine, vol. 11, pp. 271-279, 1991.
Costello et al., "Nd: YAG Laser Ablation of the Prostate as a Treatment for Benign Prostatic Hypertrophy", Lasers in Surgery and Medicine, vol. 12, pp. 121-124, 1992.
Rand et al., "Effect of Elecctrocautery on Fresh Human Articular Cartilage", J. Arthro. Surg., vol. 1, pp. 242-246, 1985.
Seal et al., "Thermal Characteristics and the Lumbar Disc: Evaluation of a Novel Approach to Targeted Intradiscal Thermal Therapy", NASS-APS First Joint Meeting, Charleston SC, Apr. 1998.
PCT International Search Report for PCT/US99/03339, 1 pg, Mailed May 14, 1999.
PCT International Search Report for PCT/US99/17821, 1 pg., Mailed Oct. 19, 1999.
PCT International Search Report for PCT/US00/13706. 1 pg., Mailed Jul. 31, 2000.
PCT International Search Report for PCT/US00/28267, 1 pg., Mailed Mar. 23, 2001.
PCT International Search Report for PCT/US01/15728, 1 pg., Mailed Oct. 18, 2001.
PCT International Preliminary Examination Report for PCT/US01/15728, 4 pgs, Jan. 23, 2003.
PCT International Search Report for PCT/US02/29469, 1 pg., Mailed May 22, 2003.
PCT International Search Report for PCT/US03/27745, 1 pg., Mailed Jul. 2, 2004.
PCT International Search Report for PCT/US05/20774 1 pg., Mailed Oct. 26, 2005.
PCT Written Opinon of the International Searching Authority for PCT/US05/20774, 4pgs., Mailed Oct. 26, 2005.
PCT International Search Report for PCT/US04/34949, 1 pg., Mailed Mar. 28, 2006.

(56) References Cited

OTHER PUBLICATIONS

PCT Written Opinon of the International Searching Authority for PCT/US04/34949, 3pgs., Mailed Mar. 28, 2006.
Supplementary EP Search Report for EP97932609, 2 pgs, Dec. 19, 2000.
EPO Communication, Supplementary EP Search Report for EP99934236, 3 pgs, Mailed Oct. 9, 2001.
EPO Communication, Supplementary EP Search Report for EP01935554, 5 pgs, Mailed Feb. 27, 2006.
EPO Communication, Supplementary EP Search Report for EP03749423, 3 pgs, Mailed Mar. 21, 2006.
EPO Communication, Supplementary EP Search Report for EP00936062, 6 pgs, Mailed Mar. 11, 2008.
PCT International Search Report and Written Opinion for PCT/US07/63198 10 pgs, Mailed Mar. 26, 2008.
EPO Communication, Supplementary EP Search Report for EP 05760511, 5 pgs, Jan. 12, 2011.
UK Search Report for GB 1108507.3 5 pgs, Sep. 23, 2011.

* cited by examiner

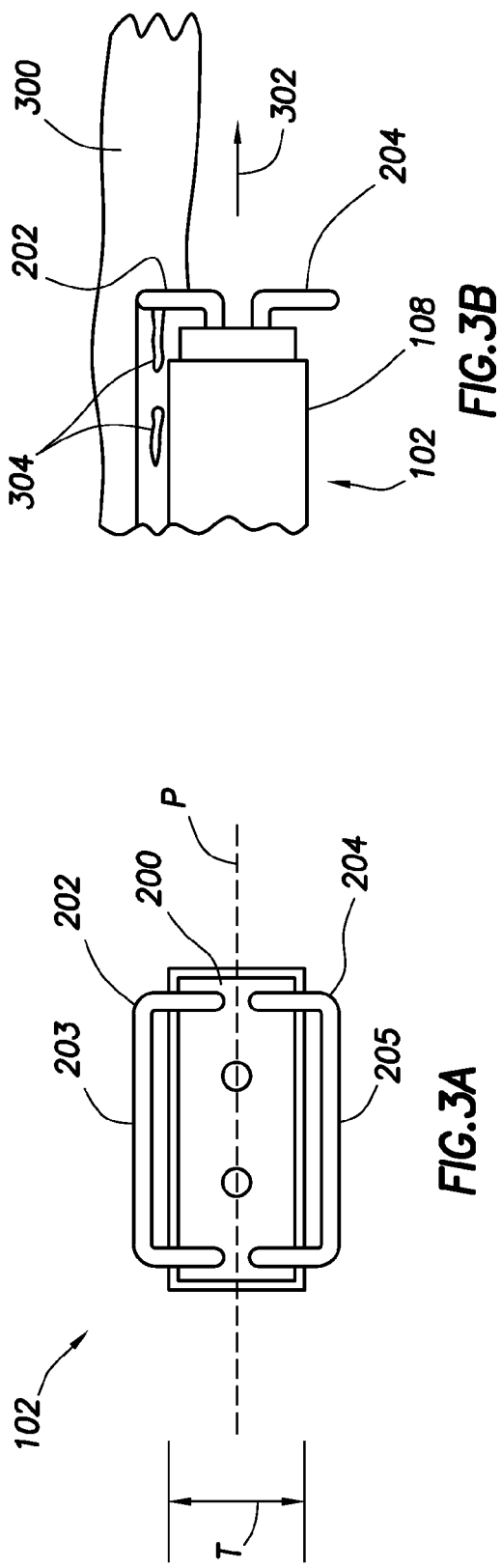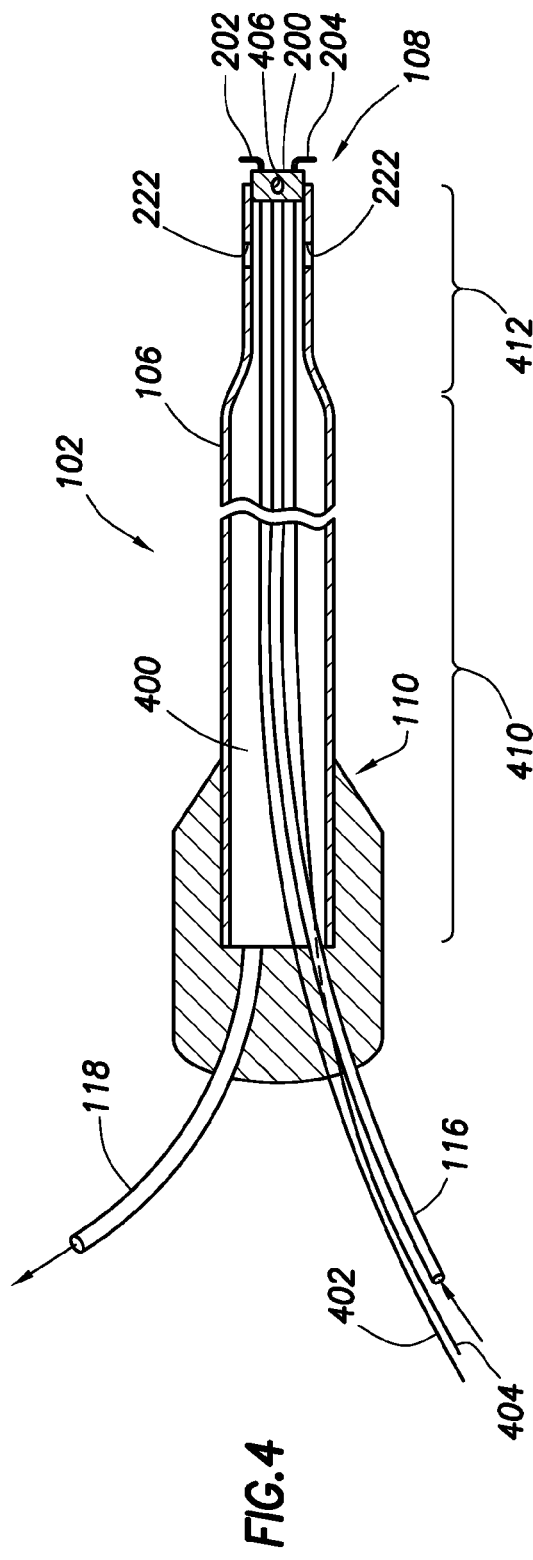

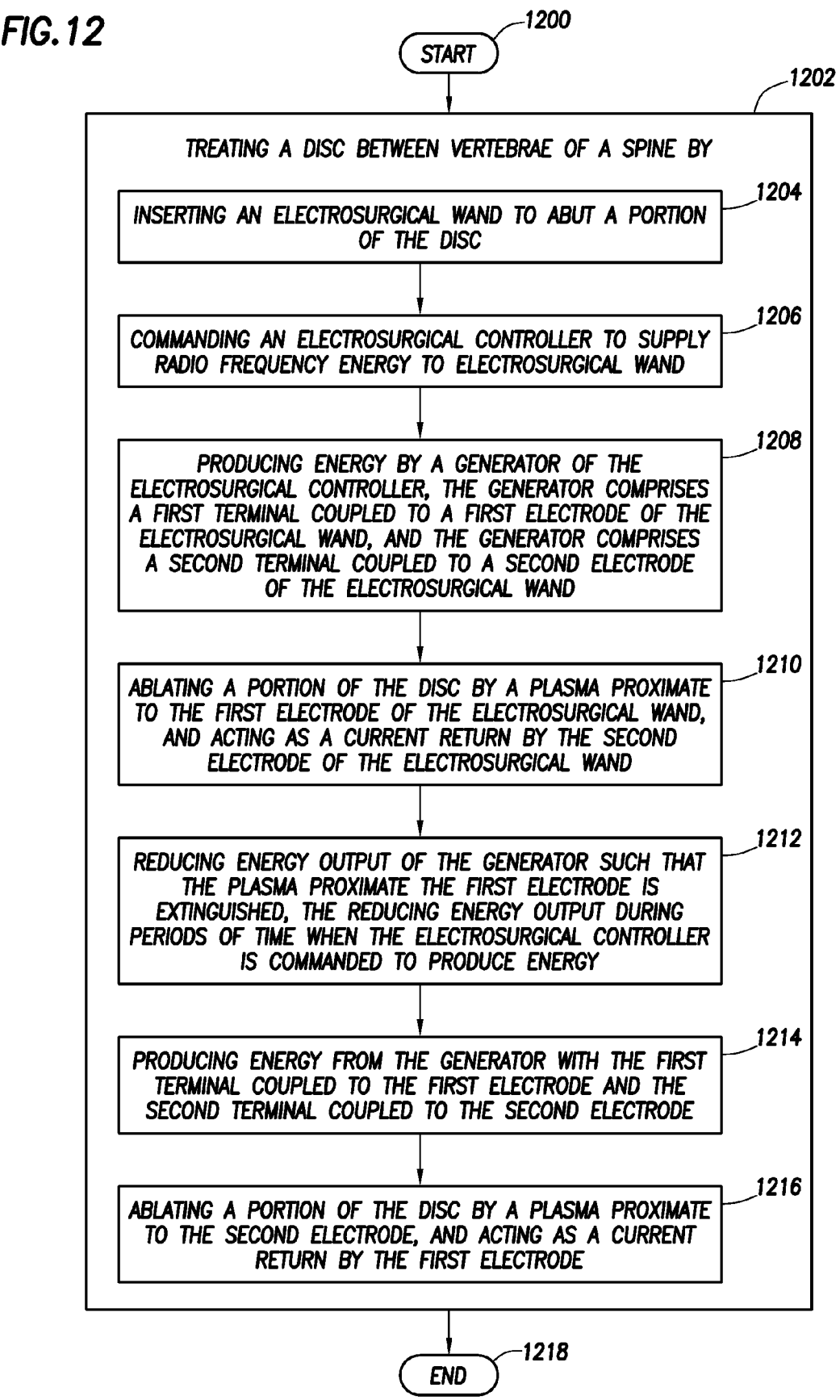

SYMMETRIC SWITCHING ELECTRODE METHOD AND RELATED SYSTEM

BACKGROUND

Electrosurgical systems are used by physicians to perform specific functions during surgical procedures. For example, electrosurgical systems use high frequency electrical energy to remove soft tissue such as sinus tissue, adipose tissue, meniscus, cartilage and/or sinovial tissue in a joint, or to remove portions of a disc between vertebrae (e.g., remove end-plate, remove annulus fibrosus).

However, the spacing between vertebrae not only limits the number and spacing of electrodes on the tip of an electrosurgical wand, but also limits the amount of movement possible with the electrosurgical wand during spinal procedures. For example, narrow spacing between the vertebrae in many cases does not allow a surgeon to turn the electrosurgical wand over with the wand tip within the disc between the vertebrae. Despite the physical limitations, both the portion of the disc near the adjacent upper vertebrae, and the portion of the disc near the adjacent lower vertebrae, may need to be treated. Having an electrosurgical wand with dedicated upper and lower active electrodes, along with a dedicated return electrode, may simultaneously treat both sides of the disc, but is impractical both because of space considerations and because having two active electrodes may cause excessive muscle and/or nerve stimulation. Having an electrosurgical wand a dedicated active electrode that only treats one side of the disc one side of the disc requires the surgeon to remove wand, turn the wand over, and re-insert the wand to treat the other side of the disc—a series of events required many times during a spinal procedure, rendering the procedure time consuming and impractical.

Any advance that makes the treatment of tissue in confined spaces faster and easier for the surgeon, and less traumatic for the patient, would provide a competitive advantage.

BRIEF DESCRIPTION OF THE DRAWINGS

For a detailed description of exemplary embodiments, reference will now be made to the accompanying drawings in which:

FIG. 3A shows an end elevation view of a wand in accordance with at least some embodiments;

FIG. 3B shows a side elevation view of a wand in accordance with at least some embodiments;

FIG. 4 shows a cross-sectional view of a wand in accordance with at least some embodiments;

FIG. 12 shows a method in accordance with at least some embodiments.

NOTATION AND NOMENCLATURE

Figure 1:
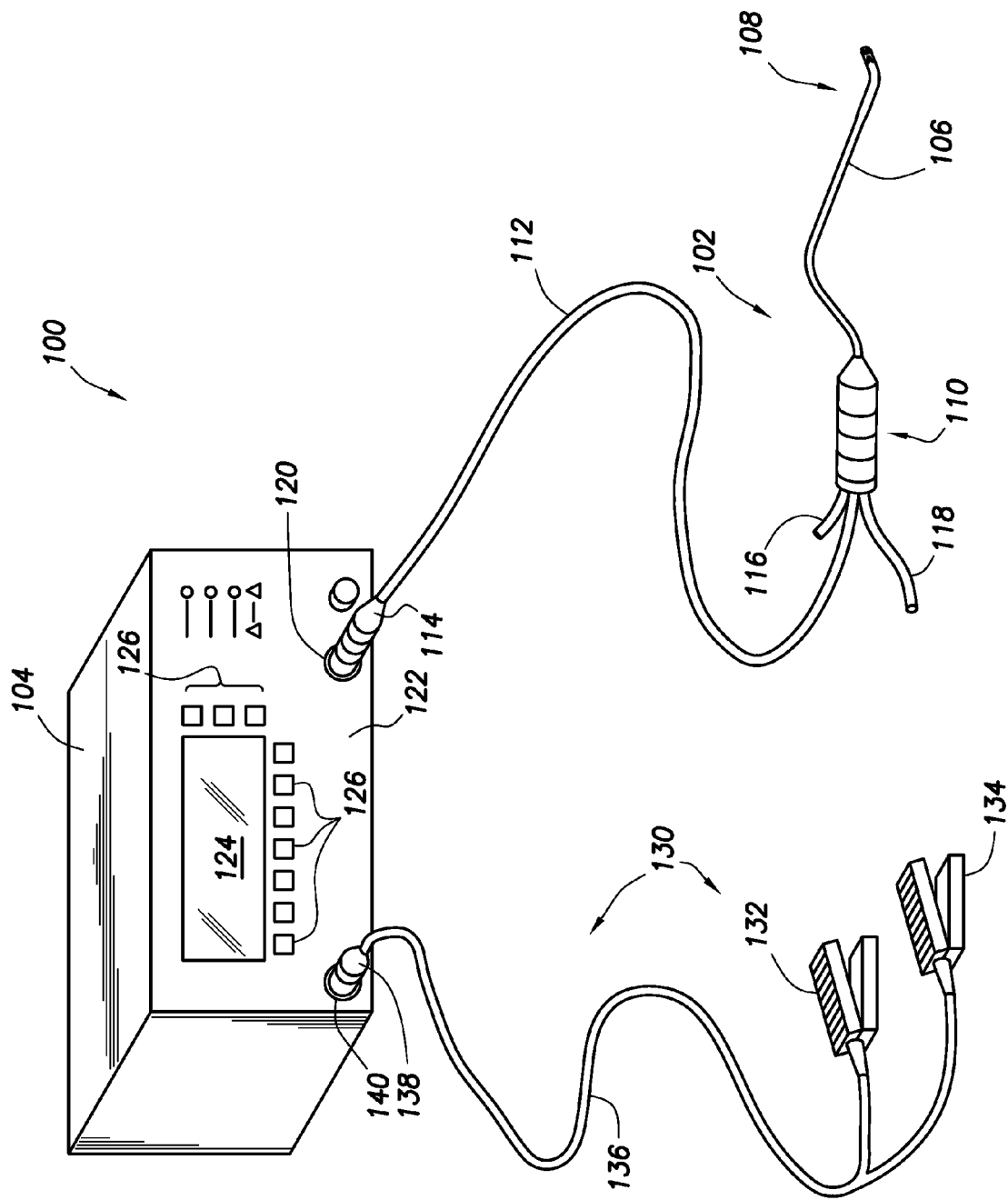
FIG. 1 shows an electrosurgical system in accordance with at least some embodiments.

Certain terms are used throughout the following description and claims to refer to particular system components. As one skilled in the art will appreciate, companies that design and manufacture electrosurgical systems may refer to a component by different names. This document does not intend to distinguish between components that differ in name but not function.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect electrical connection via other devices and connections.

Reference to a singular item includes the possibility that there are plural of the same items present. More specifically, as used herein and in the appended claims, the singular forms "a," "an," "said" and "the" include plural references unless the context clearly dictates otherwise. It is further noted that the claims may be drafted to exclude any optional element. As such, this statement serves as antecedent basis for use of such exclusive terminology as "solely," "only" and the like in connection with the recitation of claim elements, or use of a "negative" limitation. Lastly, it is to be appreciated that unless defined otherwise, all technical and scientific terms used herein have the same meaning as commonly understood by one of ordinary skill in the art to which this invention belongs.

"Active electrode" shall mean an electrode of an electrosurgical wand which produces an electrically-induced tissue-altering effect when brought into contact with, or close proximity to, a tissue targeted for treatment.

"Return electrode" shall mean an electrode of an electrosurgical wand which serves to provide a current flow path for electrons with respect to an active electrode, and/or an electrode of an electrical surgical wand which does not itself produce an electrically-induced tissue-altering effect on tissue targeted for treatment.

"Substantially", in relation to exposed surface areas, shall mean that exposed surface areas as between two electrodes are same, or differ by no more than twenty five (25) percent.

A fluid conduit said to be "within" an elongate shaft shall include not only a separate fluid conduit that physically resides within an internal volume of the elongate shaft, but also situations where the internal volume of the elongate shaft is itself the fluid conduit.

Where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

DETAILED DESCRIPTION

Before the various embodiments are described in detail, it is to be understood that this invention is not limited to particular variations set forth herein as various changes or modifications may be made, and equivalents may be substituted, without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

FIG. 1 illustrates an electrosurgical system 100 in accordance with at least some embodiments. In particular, the electrosurgical system comprises an electrosurgical wand 102 (hereinafter "wand") coupled to an electrosurgical controller 104 (hereinafter "controller"). The wand 102 comprises an elongate shaft 106 that defines distal end 108 where at least some electrodes are disposed. The elongate shaft 106 further defines a handle or proximal end 110, where a physician grips the wand 102 during surgical procedures. The wand 102 further comprises a flexible multi-conductor cable 112 housing a plurality of electrical leads (not specifically shown in FIG. 1), and the flexible multi-conductor cable 112 terminates in a wand connector 114. As shown in FIG. 1, the wand 102 couples to the controller 104, such as by a controller connector 120 on an outer surface 122 (in the illustrative case of FIG. 1, the front surface).

Though not visible in the view of FIG. 1, in some embodiments the wand 102 has one or more internal fluid conduits coupled to externally accessible tubular members. As illustrated, the wand 102 has a flexible tubular member 116 and a second flexible tubular member 118. In some embodiments, the flexible tubular member 116 is used to provide saline to the distal end 108 of the wand. Likewise in some embodiments, flexible tubular member 118 is used to provide aspiration to the distal end 108 of the wand.

Still referring to FIG. 1, a display device or interface panel 124 is visible through the outer surface 122 of the controller 104, and in some embodiments a user may select operational modes of the controller 104 by way of the interface device 124 and related buttons 126.

In some embodiments the electrosurgical system 100 also comprises a foot pedal assembly 130. The foot pedal assembly 130 may comprise one or more pedal devices 132 and 134, a flexible multi-conductor cable 136 and a pedal connector 138. While only two pedal devices 132, 134 are shown, one or more pedal devices may be implemented. The outer surface 122 of the controller 104 may comprise a corresponding connector 140 that couples to the pedal connector 138. A physician may use the foot pedal assembly 130 to control various aspects of the controller 104, such as the operational mode. For example, a pedal device, such as pedal device 132, may be used for on-off control of the application of radio frequency (RF) energy to the wand 102, and more specifically for control of energy in an ablation mode. A second pedal device, such as pedal device 134, may be used to control and/or set the operational mode of the electrosurgical system. For example, actuation of pedal device 134 may switch between energy levels of an ablation mode.

The electrosurgical system 100 of the various embodiments may have a variety of operational modes. One such mode employs Coblation® technology. In particular, the assignee of the present disclosure is the owner of Coblation® technology. Coblation® technology involves the application of a radio frequency (RF) signal between one or more active electrodes and one or more return electrodes of the wand 102 to develop high electric field intensities in the vicinity of the target tissue. The electric field intensities may be sufficient to vaporize an electrically conductive fluid over at least a portion of the one or more active electrodes in the region between the one or more active electrodes and the target tissue. The electrically conductive fluid may be inherently present in the body, such as blood, or in some cases extracelluar or intracellular fluid. In other embodiments, the electrically conductive fluid may be a liquid or gas, such as isotonic saline. In some embodiments, such as surgical procedures on a disc between vertebrae, the electrically conductive fluid is delivered in the vicinity of the active electrode and/or to the target site by the wand 102, such as by way of the internal passage and flexible tubular member 116.

When the electrically conductive fluid is heated to the point that the atoms of the fluid vaporize faster than the atoms recondense, a gas is formed. When sufficient energy is applied to the gas, the atoms collide with each other causing a release of electrons in the process, and an ionized gas or plasma is formed (the so-called "fourth state of matter"). Stated otherwise, plasmas may be formed by heating a gas and ionizing the gas by driving an electric current through the gas, or by directing electromagnetic waves into the gas. The methods of plasma formation give energy to free electrons in the plasma directly, electron-atom collisions liberate more electrons, and the process cascades until the desired degree of ionization is achieved. A more complete description of plasma can be found in Plasma Physics, by R. J. Goldston and P. H. Rutherford of the Plasma Physics Laboratory of Princeton University (1995), the complete disclosure of which is incorporated herein by reference.

As the density of the plasma becomes sufficiently low (i.e., less than approximately 1020 atoms/cm$^3$ for aqueous solutions), the electron mean free path increases such that subsequently injected electrons cause impact ionization within the plasma. When the ionic particles in the plasma layer have sufficient energy (e.g., 3.5 electron-Volt (eV) to 5 eV), collisions of the ionic particles with molecules that make up the target tissue break molecular bonds of the target tissue, dissociating molecules into free radicals which then combine into gaseous or liquid species. Often, the electrons in the plasma carry the electrical current or absorb the electromagnetic waves and, therefore, are hotter than the ionic particles. Thus, the electrons, which are carried away from the target tissue toward the active or return electrodes, carry most of the plasma's heat, enabling the ionic particles to break apart the target tissue molecules in a substantially non-thermal manner.

By means of the molecular dissociation (as opposed to thermal evaporation or carbonization), the target tissue is volumetrically removed through molecular dissociation of larger organic molecules into smaller molecules and/or atoms, such as hydrogen, oxygen, oxides of carbon, hydrocarbons and nitrogen compounds. The molecular dissociation completely removes the tissue structure, as opposed to dehydrating the tissue material by the removal of liquid within the cells of the tissue and extracellular fluids, as occurs in related art electrosurgical desiccation and vaporization. A more detailed description of the molecular dissociation can be found in commonly assigned U.S. Pat. No. 5,697,882, the complete disclosure of which is incorporated herein by reference.

In addition to the Coblation® mode, the electrosurgical system 100 of FIG. 1 may also in particular situations be useful for sealing larger arterial vessels (e.g., on the order of about 1 mm in diameter), when used in what is known as a coagulation mode. Thus, the system of FIG. 1 may have an ablation mode where RF energy at a first voltage is applied to one or more active electrodes sufficient to effect molecular dissociation or disintegration of the tissue, and the system of FIG. 1 may have a coagulation mode where RF energy at a second, lower voltage is applied to one or more active electrodes (either the same or different electrode(s) as the ablation mode) sufficient to heat, shrink, seal, fuse, and/or achieve homeostasis of severed vessels within the tissue.

The energy density produced by electrosurgical system 100 at the distal end 108 of the wand 102 may be varied by adjusting a variety of factors, such as: the number of active electrodes; electrode size and spacing; electrode surface area; asperities and/or sharp edges on the electrode surfaces; electrode materials; applied voltage; current limiting of one or more electrodes (e.g., by placing an inductor in series with an electrode); electrical conductivity of the fluid in contact with the electrodes; density of the conductive fluid; and other factors. Accordingly, these factors can be manipulated to control the energy level of the excited electrons. Since different tissue structures have different molecular bonds, the electrosurgical system 100 may be configured to produce energy sufficient to break the molecular bonds of certain tissue but insufficient to break the molecular bonds of other tissue. For example, fatty tissue (e.g., adipose) has double bonds that require an energy level higher than 4 eV to 5 eV (i.e., on the order of about 8 eV) to break. Accordingly, the Coblation® technology in some operational modes does not ablate such fatty tissue; however, the Coblation® technology at the lower energy levels may be used to effectively ablate cells to release the inner fat content in a liquid form. Other modes may have increased energy such that the double bonds can also be broken in a similar fashion as the single bonds (e.g., increasing voltage or changing the electrode configuration to increase the current density at the electrodes).

A more complete description of the various phenomena can be found in commonly assigned U.S. Pat. Nos. 6,355,032; 6,149,120 and 6,296,136, the complete disclosures of which are incorporated herein by reference.

Figure 2:
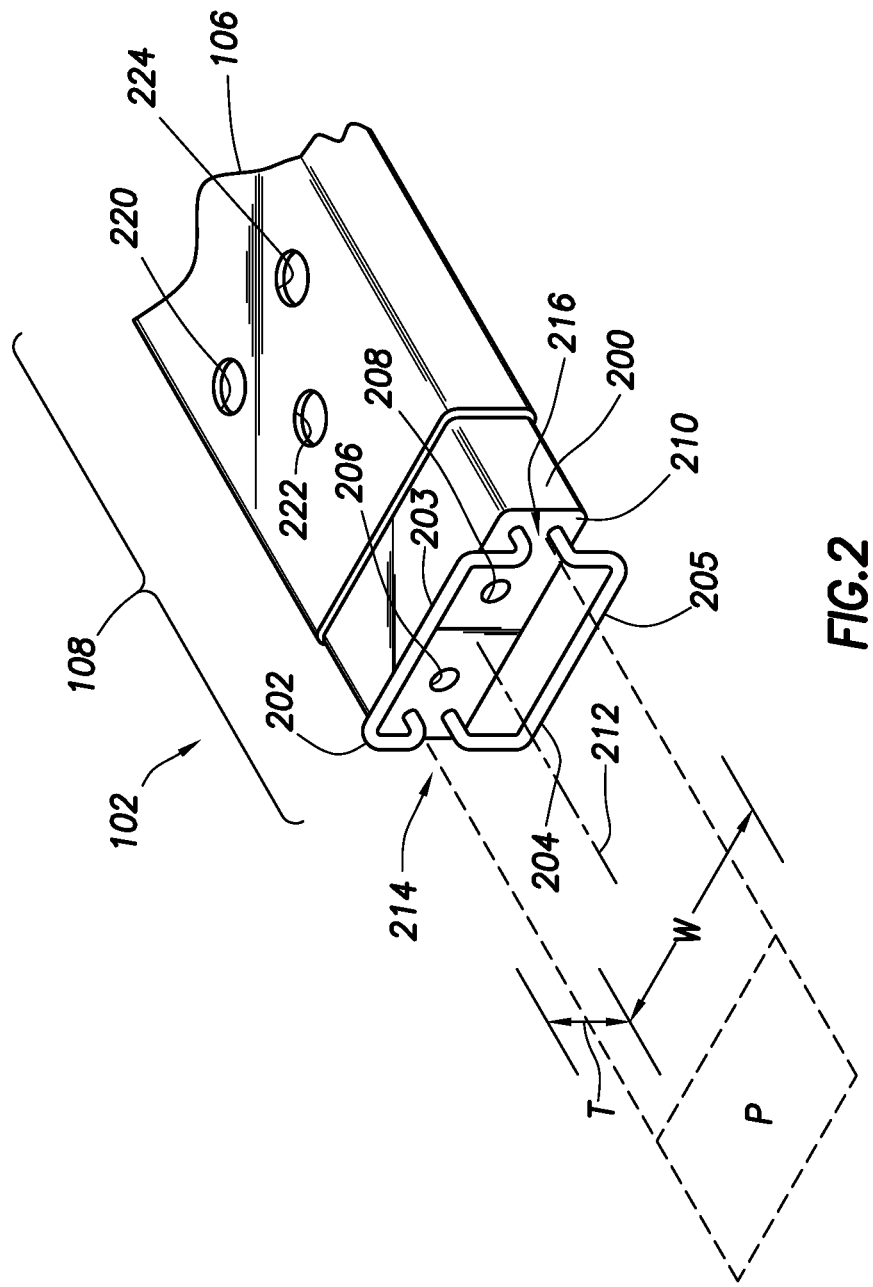
FIG. 2 shows a perspective view a portion of a wand in accordance with at least some embodiments.

FIG. 2 illustrates a perspective view of the distal end 108 of wand 102 in accordance with at least some embodiments. In particular, the distal end 108 defines a width (labeled W in the figure) and a thickness (labeled T in the figure). In some embodiments the elongate shaft 106 is made of a metallic material (e.g., Grade TP304 stainless steel hypodermic tubing). In other embodiments, the elongate shaft may be constructed of other suitable materials, such as inorganic insulating materials. For reasons that will become clear below, in at least some embodiments the metallic material of the elongate shaft 106 is not electrically grounded or electrically coupled to the generator of the controller 104. The elongate shaft 106 may define a circular cross-section at the handle or proximal end 110 (not shown in FIG. 2), and the distal end 108 may be flattened to define rectangular cross-section. In other embodiments, the flattened portion may define a semi-circular cross-section. For wands intended for use in spinal procedures, the width W may be a centimeter or less, and in some cases 5 millimeters. Likewise, for wands intended use in spinal procedures, the thickness T may be 4 millimeters or less, and in some cases 3 millimeters. Other dimensions, particularly larger dimensions, may be equivalently used when the surgical procedure allows.

In embodiments where the elongate shaft is metallic, the distal end 108 may further comprise a non-conductive spacer 200 coupled to the elongate shaft 106. In some cases the spacer 200 is ceramic, but other non-conductive materials resistant to degradation when exposed to plasma may be equivalently used (e.g., glass). The spacer 200 supports electrodes of conductive material, with illustrative electrodes labeled 202 and 204 in FIG. 2. In accordance with at least some embodiments, the upper electrode 202 is disposed above a plane that bisects the thickness (a portion of an illustrative plane that bisects the thickness labeled P in FIG. 2), and with the lower electrode 204 disposed below the plane that bisects the thickness.

Each electrode 202 and 204 defines an exposed surface area of conductive material, and in accordance with at least some embodiments the exposed surface area as between the upper electrode 202 and the lower electrode 204 is substantially the same. In the particular embodiment of FIG. 2, each electrode 202 and 204 is a loop of wire of particular diameter. The wire diameter selected for a particular wand depends, at least in part, on the parasitic stimulation of muscle and/or nerves that can be tolerated by the particular medical procedure. Greater parasitic stimulation is present with greater exposed surface areas of the conductors (i.e., greater wire diameters and length), and less parasitic stimulation is present with less exposed surface area (i.e., smaller wire diameters and lengths). However, as wire diameters decrease, the wires become more fragile and subject to bending or breaking. For embodiments using loops of wire such as in FIG. 2, the wire diameter may be between and including 0.008 inches to 0.015 inches. In a particular embodiment for removal of intervertebral disc material (e.g., for discectomy procedures in order to perform interbody vertebral fusion), the loops of wire may be tungsten having a diameter of 0.012 inches and have an exposed length of approximately 0.228 inches.

In accordance with at least some embodiments, not only do the electrodes define substantially the same exposed surface area as between the upper and lower electrodes, but also the shape as between the upper and lower electrodes is symmetric. In particular, the upper electrode 202 defines a particular shape, and likewise the lower electrode defines a particular shape. The shapes defined by the electrodes 202 and 204 are symmetric about the plane P that bisects the thickness T. More particularly still, in some embodiments the electrodes 202 and 204 are mirror images of each other reflected about the plane P that bisects the thickness. In other embodiments, the shape of the electrodes may be non-symmetrical about the plane P, even if the exposed surface areas are substantially the same.

Still referring to FIG. 2, the illustrative wire loop electrodes 202 and 204 each define a straight portion 203 and 205, respectively. In at least some embodiments, each straight portion 203 and 205 are parallel to the plane P that bisects the thickness of the distal end 108. In embodiments where the electrodes are symmetric, the straight portions 203 and 205 are likewise parallel to each other. However, in other embodiments the straight portions 203 and 205 are each be parallel to the plane P, but not necessarily parallel to each other.

In some embodiments saline is delivered to the distal end 108 of wand, possibly to aid in plasma creation. Still referring to FIG. 2, FIG. 2 illustrates discharge apertures 206 and 208 on the distal end 108 between the electrodes 202 and 204. In the particular embodiment illustrated, two discharge apertures are shown, but one or more discharge apertures are contemplated. The discharge apertures 206 and 208 are fluidly coupled to the flexible tubular member 116 (FIG. 1) by way of a fluid conduit within the wand 102. Thus, saline or other fluid may be pumped into the flexible tubular member 116 (FIG. 1) and discharge through the discharge apertures 206 and 208. In some cases, the fluid may discharge straight out of each discharge aperture 206 and 208 (i.e., normal to the front surface 210 of the spacer 200), but in other cases the fluid may discharge at an angle. Consider that the distal end 108 of the wand 102 defines a wand tip axis 212. In a particular embodiment, each discharge aperture 206 and 208 is created and/or formed to direct discharging fluid out the aperture a non-zero angle relative to the wand tip axis 212. For example, the discharge aperture 206 may direct discharging fluid toward the bends 214 in the wire loop electrodes 202 and 204. Likewise, the discharge aperture 208 may direct discharging fluid toward the bends 216 in the wire loop electrodes 202 and 204. The inventors of the present specification have found that discharging the fluid from the apertures at a non-zero angle appears to aid plasma creation. The discharge apertures are relatively small, on the order of 1 millimeter or less. During spinal procedures, between and 10 and 60 milli-Liters (mL) per second (mL/s) total flows from the discharge apertures, and in particular cases 30 mL/s flows. Other flow volumes are contemplated for different procedures, with the amount of fluid flow through the apertures dependent upon the amount of fluid naturally present at the surgical site of the body.

In yet still further embodiments, aspiration is provided at the distal end 108 of the wand 102. FIG. 2 illustrates aspiration apertures 220, 222 and 224. While three such aspiration apertures are shown, one or more aspiration apertures are contemplated. Though not visible in the view of FIG. 2, in some case three or more additional aspiration apertures are present on the bottom side of the distal end 108. The aspiration apertures 220, 222 and 224 are disposed on the distal end 108, but as illustrated the aspiration apertures are closer to the proximal end 110 (FIG. 1) of the wand 102 than the discharge apertures 206 and 208. The aspiration apertures are fluidly coupled to flexible tubular member 118 (FIG. 1), possibly by way of a fluid conduit within the wand 102. In a particular embodiment, the flexible tubular member 118 resides within the handle of the proximal end 110 (FIG. 1) of the wand 102, but then seals to the elongate shaft 106 in such a way that the elongate shaft 106 itself becomes a portion of the fluid conduit for the aspiration apertures. The aspiration apertures 220, 222 and 224 aspirate the area near the distal end 108, such as to remove excess fluids and remnants of ablation. The aspiration apertures 220, 222 and 224 are disposed as close to the electrodes 202 and 204 as assembly considerations will allow, and in many cases 5 centimeters or less.

FIG. 3A illustrates an elevational end-view of the distal end 108 of the illustrative wand 102 in order to show further relationships of the electrodes 202 and 204. As discussed with respect to FIG. 2, the illustrative wire loop electrode 202 resides above a plane P that bisects the thickness T, and in the view of FIG. 3 plane P appears only as a line segment (shown in dashed form). Likewise, the illustrative wire loop electrode 204 resides below the plane P that bisects the thickness T. As discussed above, each of the illustrative wire loop electrodes 202 and 204 define a straight portion 203 and 205, respectively. FIG. 3 illustrates that, in at least some embodiments, the straight portion 203 of wire loop 202 resides above the plane P by more than half the thickness T. Likewise, the straight portion 205 of wire loop 204 resides below the plane P by more than half the thickness T. Stated otherwise, the physical relationship of the straight portions 203 and 205 to the balance of the distal end 108 is that each straight portion resides outside a boundary defined by the elongate shaft 106 and/or the spacer 200. Although not required in every case, the physical placement of the straight portions 203 and 205 relative to the elongate shaft 106 and/or the spacer 200 provides a useful feature in ablation in accordance with at least some embodiments.

Having the straight portions 203 and 205 residing outside a boundary defined by the elongate shaft 106 and/or spacer 200 provides an operational aspect where tissue to be removed is not removed by being fully ablated; rather, the physical relationship enables "slicing" of the tissue. FIG. 3B illustrates a side elevation view of the distal end 108 of the wand 102 in illustrative relation to tissue 300 to be removed. In particular, consider that plasma has been created near electrode 202. As the wand 102 moves in the direction illustrated by arrow 302, portions of the tissue 300 are "sliced" off the larger tissue portion 300. The "slicing" action itself may be by ablation of some of the tissue, but portions of the tissue are separated from the larger portion by the "slicing" action, as illustrated by portions 304. These portions 304 may be removed from the treatment area by the aspiration provided through aspiration ports (not visible in FIG. 3B). Although illustrative FIG. 3B shows the "slicing" action in only one direction, the "slicing" action may take place in the opposite direction as well. Moreover, while illustrative FIG. 3B shows the "slicing" action only with respect to electrode 202, the "slicing" action may likewise take place with respect to electrode 204.

FIG. 4 shows a cross-sectional elevation view of a wand 102 in accordance with at least some embodiments. In particular, FIG. 4 shows the handle or proximal end 110 coupled to the elongate shaft 106. As illustrated, the elongate shaft 106 telescopes within the handle, but other mechanisms to couple the elongate shaft to the handle may be equivalently used. The elongate shaft 106 defines internal conduit 400 that serves several purposes. For example, in the embodiments illustrated by FIG. 4 the electrical leads 402 and 404 extend through the internal conduit 400 to electrically couple to the electrodes 202 and 204, respectively. Likewise, the flexible tubular member 116 extends through the internal conduit 400 to fluidly couple to the apertures 206 and 208 (not visible in FIG. 4, but a fluid pathway 406 within the spacer 200 is visible).

The internal conduit 400 also serves as the aspiration route. In particular, FIG. 4 illustrates aspiration apertures 222 (one on top and another on bottom). In the embodiments illustrated, the flexible tubular member 118, through which aspiration is performed, couples through the handle and then fluidly couples to the internal conduit 400. Thus, the suction provided through flexible tubular member 118 provides aspiration at the aspiration apertures 222 (and others not visible). The fluids that are drawn into the internal fluid conduit 400 may abut the portion of the flexible tubular member 116 that resides within the internal conduit as the fluids are drawn along the conduit; however, the flexible tubular member 116 is sealed, and thus the aspirated fluids do not mix with the fluid (e.g., saline) being pumped through the flexible tubular member 116. Likewise, the fluids that are drawn into the internal fluid conduit 400 may abut portions of the electrical leads 402 and 404 within the internal fluid conduit 400 as the fluids are drawn along the conduit. However, the electrical leads are insulated with an insulating material that electrically and fluidly isolates the leads from any substance within the internal fluid conduit 400. Thus, the internal fluid conduit serves, in the embodiments shown, two purposes—one to be the pathway through which the flexible tubular member 116 and electrical leads traverse to reach the distal end 108, and also as the conduit through which aspiration takes place. In other embodiments, the flexible tubular member 118 may extend partially or fully through the elongate shaft 106, and thus more directly couple to the aspiration apertures.

FIG. 4 also illustrates that, in accordance with at least some embodiments, a portion of the elongate shaft 106 is circular (e.g., portion 410) and another portion of the elongate shaft 106 is flattened (e.g., portion 412) to define a rectangular or semi-circular cross-section. In some embodiments, the distal 6 centimeters or less is flattened, and in some cases the last 4 centimeters. In other embodiments, the entire elongate shaft may define the rectangular or semi-circular cross-section. The offsets of the elongate shaft 106 are not visible in FIG. 4 because of the particular view; however, FIG. 5 shows illustrative offsets.

Figure 5:
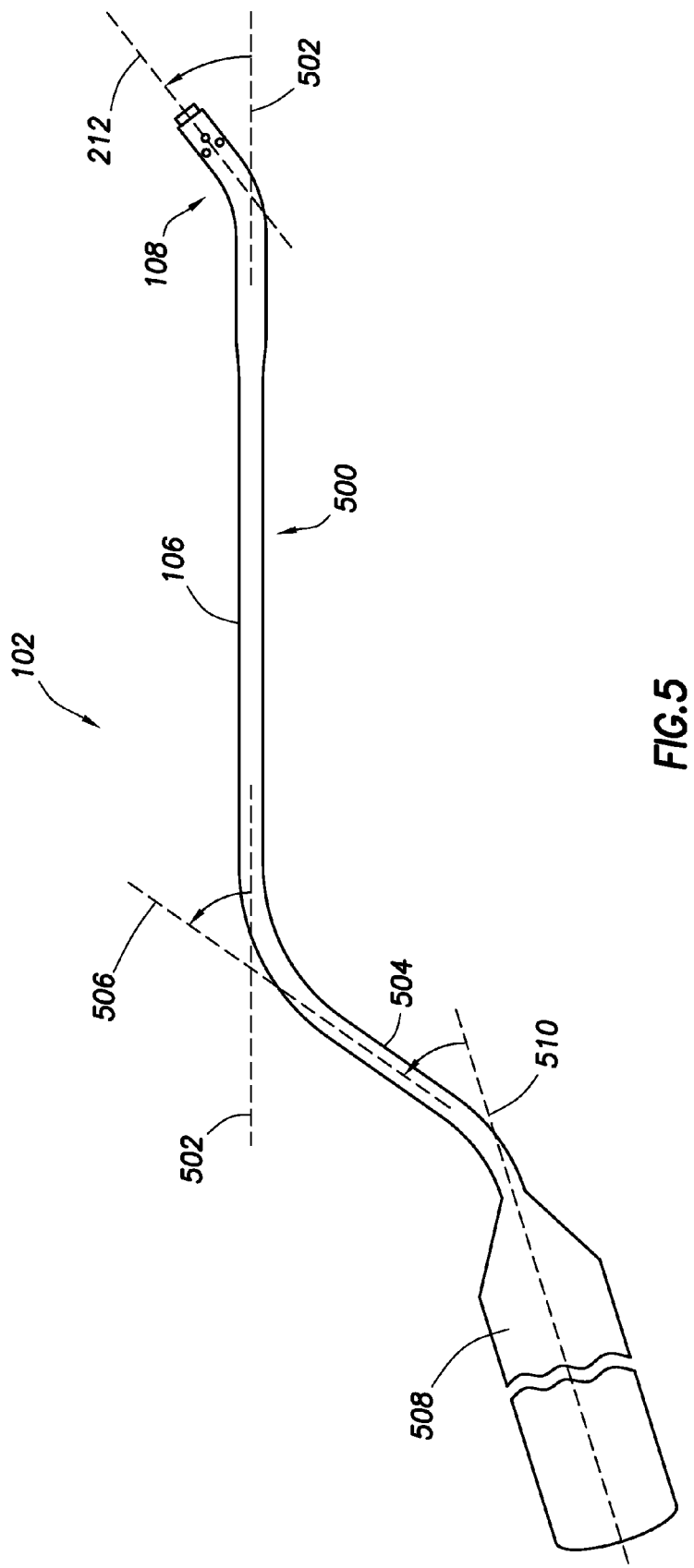
FIG. 5 shows an overhead view of a wand in accordance with at least some embodiments.

FIG. 5 shows an overhead view of the wand 102 in an orientation where the offsets in the elongate shaft 106 are visible. The illustrative wand 102 is designed and constructed for use in procedures where other equipment (e.g., an arthoscopic camera or surgical microscope) may be present and where those other devices prevent use of straight elongate shaft. In particular, the distal end 108 defines wand tip axis 212, and the elongate shaft 106 also defines a medial portion 500 which has an axis 502 (hereafter, the medial axis 502). In the particular embodiments illustrated the angle between the medial axis 502 and the wand tip axis 212 is non-zero, and in some embodiments the acute angle between the medial axis 502 and the wand tip axis is 35 degrees, but greater or lesser angles may be equivalently used.

Likewise, the elongate shaft 106 of FIG. 5 defines a proximal portion 504 with an axis 506 (hereafter, the proximal axis 506). In the particular embodiment illustrated the angle between the proximal axis 506 and the medial axis 502 is non-zero, and in some embodiments the acute angle between the proximal axis 506 and the medial axis 502 is 55 degrees, but greater or lesser angles may be equivalently used. Further still, the handle 508 of FIG. 5 defines an axis 510 (hereafter, the handle axis 510). In the particular embodiment illustrated the acute angle between the handle axis 510 and the proximal axis 506 is non-zero, and in some embodiments the acute angle between the handle axis 510 and the medial axis 506 is 40 degrees, but greater or lesser angles may be equivalently used.

Figure 6:
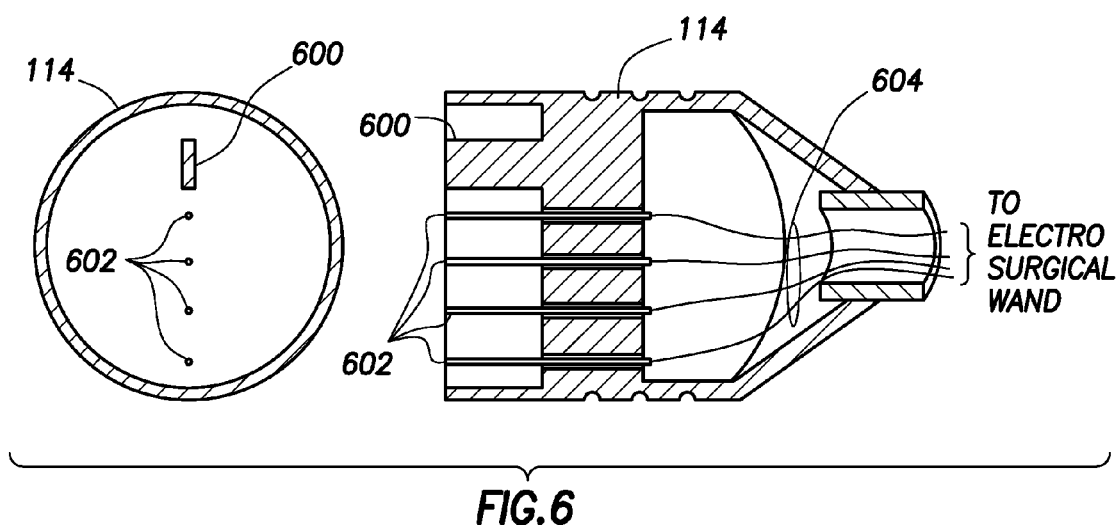
FIG. 6 shows both an elevational end-view (left) and a cross-sectional view (right) of a wand connector in accordance with at least some embodiments.

As illustrated in FIG. 1, flexible multi-conductor cable 112 (and more particularly its constituent electrical leads 402, 404 and possibly others) couple to the wand connector 114. Wand connector 114 couples the controller 104, and more particularly the controller connector 120. FIG. 6 shows both a cross-sectional view (right) and an end elevation view (left) of wand connector 114 in accordance with at least some embodiments. In particular, wand connector 114 comprises a tab 600. Tab 600 works in conjunction with a slot on controller connector 120 (shown in FIG. 7) to ensure that the wand connector 114 and controller connector 120 only couple in one relative orientation. The illustrative wand connector 114 further comprises a plurality of electrical pins 602 protruding from wand connector 114. In many cases, the electrical pins 602 are coupled one each to an electrical lead of electrical leads 604 (two of which may be leads 402 and 404 of FIG. 4). Stated otherwise, in particular embodiments each electrical pin 602 couples to a single electrical lead, and thus each illustrative electrical pin 602 couples to a single electrode of the wand 102. In other cases, a single electrical pin 602 couples to multiple electrodes on the electrosurgical wand 102. While FIG. 6 shows four illustrative electrical pins, in some embodiments as few as two electrical pins, and as many as 26 electrical pins, may be present in the wand connector 114.

Figure 7:
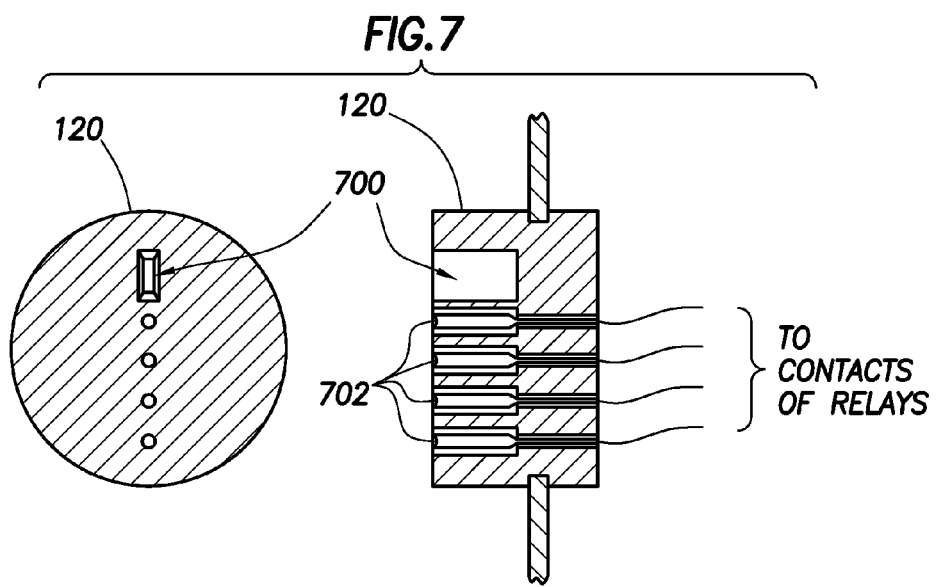
FIG. 7 shows both an elevational end-view (left) and a cross-sectional view (right) of a controller connector in accordance with at least some embodiments.

FIG. 7 shows both a cross-sectional view (right) and an end elevation view (left) of controller connector 120 in accordance with at least some embodiments. In particular, controller connector 120 comprises a slot 700. Slot 700 works in conjunction with a tab 600 on wand connector 114 (shown in FIG. 6) to ensure that the wand connector 114 and controller connector 120 only couple in one orientation. The illustrative controller connector 120 further comprises a plurality of electrical pins 702 residing within respective holes of controller connector 120. The electrical pins 702 are coupled to terminals of a voltage generator within the controller 104 (discussed more thoroughly below). When wand connector 114 and controller connector 120 are coupled, each electrical pin 702 couples to a single electrical pin 602. While FIG. 7 shows only four illustrative electrical pins, in some embodiments as few as two electrical pins, and as many as 26 electrical pins may be present in the wand connector 120.

While illustrative wand connector 114 is shown to have the tab 600 and male electrical pins 602, and controller connector 120 is shown to have the slot 700 and female electrical pins 702, in alternative embodiments the wand connector has the female electrical pins and slot, and the controller connector 120 has the tab and male electrical pins, or other combination. In other embodiments, the arrangement of the pins within the connectors may enable only a single orientation for connection of the connectors, and thus the tab and slot arrangement may be omitted. In yet still other embodiments, other mechanical arrangements to ensure the wand connector and controller connector couple in only one orientation may be equivalently used. In the case of a wand with only two electrodes, and which electrodes may be either active or return electrodes as the physical situation dictates, there may be no need to ensure the connectors couple in a particular orientation.

Figure 8:
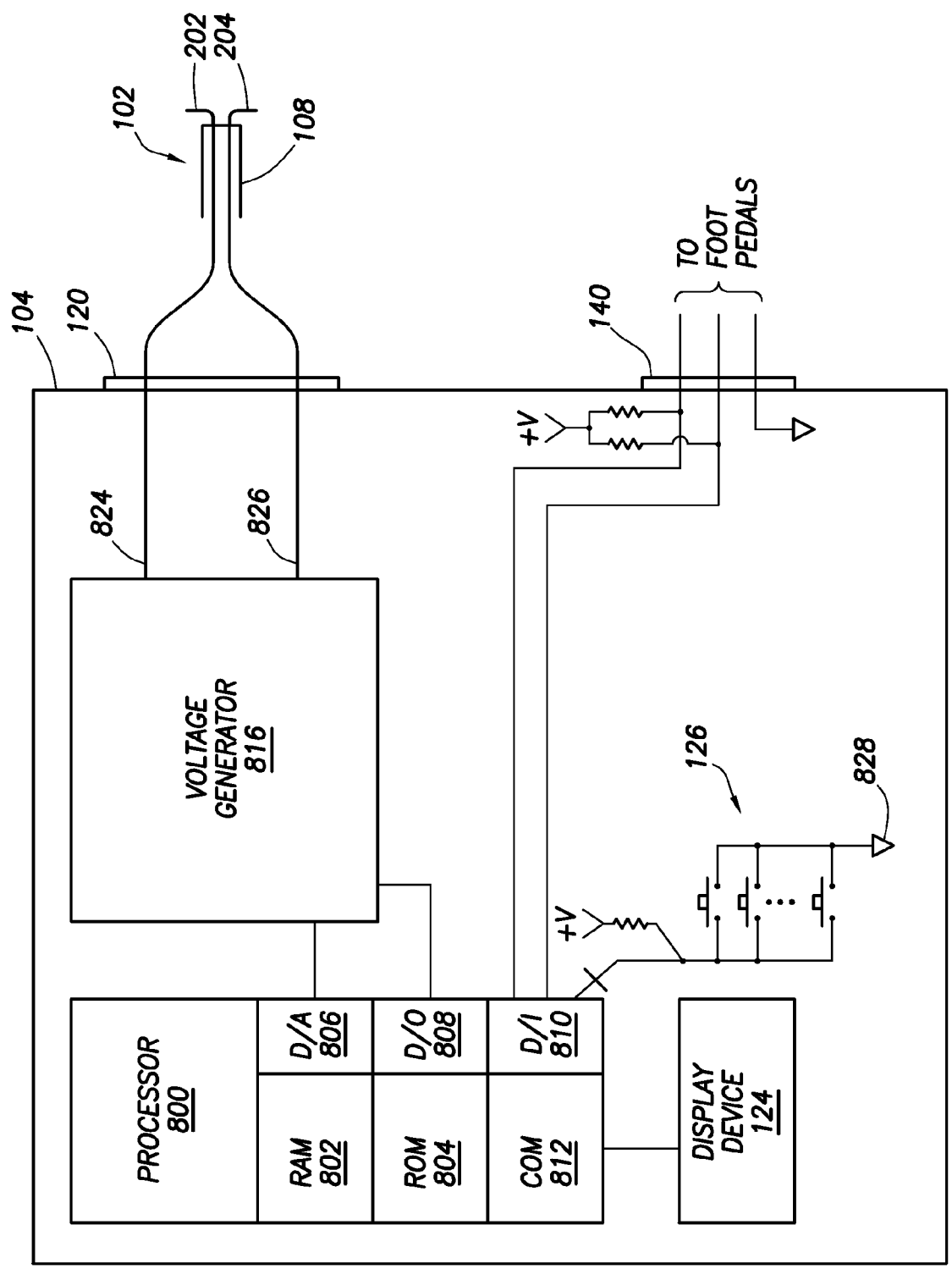
FIG. 8 shows an electrical block diagram of an electrosurgical controller in accordance with at least some embodiments.

FIG. 8 illustrates a controller 104 in accordance with at least some embodiments. In particular, the controller 104 comprises a processor 800. The processor 800 may be a microcontroller, and therefore the microcontroller may be integral with random access memory (RAM) 802, read-only memory (RAM) 804, digital-to-analog converter (D/A) 806, digital outputs (D/O) 808 and digital inputs (D/I) 810. The processor 800 may further provide one or more externally available peripheral busses, such as a serial bus (e.g., I²C), parallel bus, or other bus and corresponding communication mode. The processor 800 may further be integral with a communication logic 812 to enable the processor 800 to communicate with external devices, as well as internal devices, such as display deice 124. Although in some embodiments the controller 104 may implement a microcontroller, in yet other embodiments the processor 800 may be implemented as a standalone central processing unit in combination with individual RAM, ROM, communication, D/A, D/O and D/I devices, as well as communication port hardware for communication to peripheral components.

ROM 804 stores instructions executable by the processor 800. In particular, the ROM 804 may comprise a software program that implements the various embodiments of periodically reducing voltage generator output to change position of the plasma relative to the electrodes of the wand (discussed more below), as well as interfacing with the user by way of the display device 124 and/or the foot pedal assembly 130 (FIG. 1). The RAM 802 may be the working memory for the processor 800, where data may be temporarily stored and from which instructions may be executed. Processor 800 couples to other devices within the controller 104 by way of the D/A converter 806 (e.g., the voltage generator 816), digital outputs 808 (e.g., the voltage generate 816), digital inputs 810 (i.e., push button switches 126, and the foot pedal assembly 130 (FIG. 1)), and other peripheral devices.

Voltage generator 816 generates selectable alternating current (AC) voltages that are applied to the electrodes of the wand 102. In the various embodiments, the voltage generator defines two terminals 824 and 826. In accordance with the various embodiments, the voltage generator generates an alternating current (AC) voltage across the terminals 824 and 826. In at least some embodiments the voltage generator 816 is electrically "floated" from the balance of the supply power in the controller 104, and thus the voltage on terminals 824, 826, when measured with respect to the earth ground or common (e.g., common 828) within the controller 104, may or may not show a voltage difference even when the voltage generator 816 is active.

The voltage generated and applied between the active terminal 624 and return terminal 626 by the voltage generator 616 is a RF signal that, in some embodiments, has a frequency of between about 5 kilo-Hertz (kHz) and 20 Mega-Hertz (MHz), in some cases being between about 30 kHz and 2.5 MHz, often between about 100 kHz and 200 kHz. In applications near the spine, a frequency of about 100 kHz appears most therapeutic. The RMS (root mean square) voltage generated by the voltage generator 816 may be in the range from about 5 Volts (V) to 1000 V, preferably being in the range from about 10 V to 500 V, often between about 100 V to 350 V depending on the active electrode size and the operating frequency. The peak-to-peak voltage generated by the voltage generator 816 for ablation or cutting in some embodiments is a square wave form in the range of 10 V to 2000 V and in some cases in the range of 100 V to 1800 V and in other cases in the range of about 28 V to 1200 V, often in the range of about 100 V to 320V peak-to-peak (again, depending on the electrode size and the operating frequency).

Still referring to the voltage generator 816, the voltage generator 816 delivers average power levels ranging from several milliwatts to hundreds of watts per electrode, depending on the voltage applied for the target tissue being treated, and/or the maximum allowed temperature selected for the wand 102. The voltage generator 816 is configured to enable a user to select the voltage level according to the specific requirements of a particular procedure. A description of one suitable voltage generator 816 can be found in commonly assigned U.S. Pat. Nos. 6,142,992 and 6,235,020, the complete disclosure of both patents are incorporated herein by reference for all purposes.

In some embodiments, the various operational modes of the voltage generator 816 may be controlled by way of digital-to-analog converter 806. That is, for example, the processor 800 may control the output voltage by providing a variable voltage to the voltage generator 816, where the voltage provided is proportional to the voltage generated by the voltage generator 816. In other embodiments, the processor 800 may communicate with the voltage generator by way of one or more digital output signals from the digital output 808 device, or by way of packet based communications using the communication device 812 (connection not specifically shown so as not to unduly complicate FIG. 8).

FIG. 8 also shows a simplified side view of the distal end 108 of the wand 102. As shown, illustrative electrode 202 of the wand 102 electrically couples to terminal 824 of the voltage generator 816 by way of the connector 120, and electrode 204 electrically couples to terminal 826 of the voltage generator 816.

As alluded to above, in certain electrosurgical procedures, such as discectomy procedures, it may not be possible to turn the wand 102 over when the distal end 108 is within a disc (i.e., the distance between vertebrae is smaller than the width of the wand); however, the surgical effect desired (e.g., ablation) may need to be applied to an upper portion of the disc, then a lower portion of the disc, and so on, as the distal end 108 of the wand moves within the disc. The various embodiments address the difficulties noted by a combination of an operational mode of the controller 104 and the relationship of illustrative electrodes 202 and 204. The operational mode of the controller 104 and relationship of the electrodes 202 and 204 will be discussed after a short digression into characteristics plasma creation and continuance.

In particular, in situations where plasma has yet to form but could form around any one of multiple electrodes, plasma tends to form in areas of highest current density. For example, as between two illustrative electrodes having the same exposed surface area of conductive material and same applied RMS voltage, during periods of time when RF energy is being applied across the electrodes but before plasma creation, the highest current density forms near the electrode closest to tissue of the patient. However, once plasma is formed a reduction in applied RF energy (to a point) will not necessarily extinguish the plasma, even in situations where another electrode would facilitate a higher current density if plasma creation was started anew.

In accordance with the various embodiments, a controller 104 is operated in a manner where plasma is created near a first electrode, and thus ablation takes place for a period of time, and then the plasma is extinguished (e.g., by a sufficient reduction in RF energy applied to the electrodes). Thereafter, the RF energy is again applied and thus plasma is created near whichever electrode produces the highest current density. Under the assumption that the ablation caused by the first plasma proximate to the first electrode removed tissue near the first electrode, when the RF energy is again applied in all likelihood the second electrode will then be closer to tissue than the first electrode, and thus the highest current density will be present near the second electrode and the plasma will be created near the second electrode.

More specifically, and in reference again to FIG. 8, in accordance with embodiments discussed above, the electrodes 202 and 204 have substantially the same exposed surface area of conductive material and also are symmetrically shaped. Voltage generator 816 initially applies RF energy across the terminals 824 and 826, and that RF energy is coupled to the electrodes 202 and 204. A plasma forms in the area of highest current density. For purposes of discussion, consider that the area of highest current density is initially near the electrode 202. Thus, plasma will initially form near the electrode 202 (meaning that electrode 202 becomes the active electrode), and electrode 204 acts as a current return for the plasma (meaning that electrode 204 becomes the return electrode). After a predetermined period of time, the controller 104 reduces the RF energy output from the voltage generator 816 by an amount sufficient to extinguish the plasma, the reduction for a predetermined period of time, and then the voltage generator 816 again applies RF energy across the terminals 824 and 826. Now consider that because of ablation that took place near the electrode 202, when the RF energy is produced again the area of highest current density is near electrode 204. Thus, plasma will form near the electrode 204 (meaning that electrode 204 becomes the active electrode), and electrode 202 acts as a current return for the plasma (meaning that electrode 202 becomes the return electrode). The cycle of producing energy, creating a plasma near an electrode, reducing energy sufficient to extinguish the plasma, and producing energy is repeated for extended periods of time. Thus, as the distal end 108 of the wand 102 is pushed through a disc, ablation takes places separately near each electrode, and in some cases (though not necessarily) alternately between the upper electrode 202 and lower electrode 204.

In the various embodiments the RF energy is applied for a predetermined period of time, in some cases between and including 50 milliseconds (ms) and 2000 ms, and in some cases 500 ms. As for reduction of RF energy sufficient to extinguish the plasma, in some cases the RF energy is reduced to zero (i.e., the voltage generator is turned off), but in other cases the RF energy remains non-zero, but is reduced an amount sufficient to extinguish the plasma where the amount of reduction is dependent upon the specific electrode configuration (e.g., in a particular electrode configuration a 50% reduction in RF energy may be sufficient). In some cases, the RF energy is reduced for at least 20 ms, and in some cases 50 ms. Before proceeding it should be understood that the RF energy applied across the terminals 824 and 826, and thus applied across the electrodes 202 and 204, is an AC voltage. By definition, and AC voltage swings from a positive value to a negative value, including a zero-crossing; however, changes in voltage associated with an applied AC waveform (e.g., sinusoidal, square) shall not be considered a "reduction" in voltage for purposes of this disclosure and claims.

In accordance with at least some embodiments, the cycle of producing RF energy at a particular level, reducing the RF energy, and then producing the RF energy again is an automatic function of the controller 104. Stated otherwise, once selected as the operational mode (e.g., by actuation of a foot pedal device, by interaction with switches 126, or possibly by wand specific inputs from the wand connector) when operated in the mode described the surgeon need not take action during the procedure to facilitate the cycle; rather, the cycle takes place during periods of time when the controller 104 is commanded to produce RF energy. Consider, as a specific example, a surgeon performing a discectomy. The surgeon selects an operational mode (e.g., by the switches 126), then commands production of RF energy by stepping on and holding down foot pedal device 132. In other words, stepping on and holding the foot pedal device indicates a command to produce energy. While the foot pedal device is depressed (i.e., while the controller 104 is commanded to produce RF energy), the RF energy IS produced, reduced, and re-produced in the cycle described above many times per second. Stated otherwise, in spite of the fact the surgeon has commanded the controller 104 to produce energy, the controller 104 may nevertheless reduce the RF energy, and in some cases turn the RF energy off, to extinguish the plasma as described above. Stated otherwise yet further still, forming the plasma proximate the first electrode, and then forming the plasma proximate the second electrode, is in the absence of a command provided to the electrosurgical controller to change an active electrode.

Thus, an aspect of operation is enabling the plasma to form proximate to an electrode closest to the tissue to be treated. So as not to favor one electrode over another for purposes of plasma creation, the electrodes in accordance with at least some embodiments have equal or substantially equal exposed surface areas. Moreover, when plasma forms near one electrode that electrode becomes an active electrode, while the other electrode becomes a return electrode, and their roles reverse periodically. So that each electrode has a fair opportunity to be either the active or return electrode, in embodiments where the elongate shaft 106 is metallic the elongate shaft is not electrically grounded or electrically coupled to the generator 104. Stated otherwise, having an electrically grounded metallic elongate shaft may interfere with the plasma creation aspects.

The cycle of production of energy, reduction of energy, and re-production of energy may be implemented in many forms. For example, in some cases when a particular operational mode is selected for the controller 104, the processor 800 executes a program that periodically commands the voltage generator 816 to reduce the RF energy (again, the reduction in some cases to zero) in order to extinguish the plasma. In yet still other embodiments, the voltage generator 816 itself may implement circuitry to perform the cycle as discussed.

Returning briefly to FIG. 3B, FIG. 3B shows the "slicing" effect of the illustrative wire loop electrodes. In relation to the cyclic plasma creation, it can now be pointed out that, as a wand 102 is pushed through a target tissue like a disc between vertebrae, the "slicing" action may take place with respect to the upper electrode 202, then because of the substantially similarity of the exposed surface areas of the conductive material, and the ablated tissue near the upper electrode, when plasma is created anew that plasma will in all likelihood be created near the lower electrode 204 (though the tissue near the lower electrode 204 is not shown in FIG. 3B).

Figure 9:
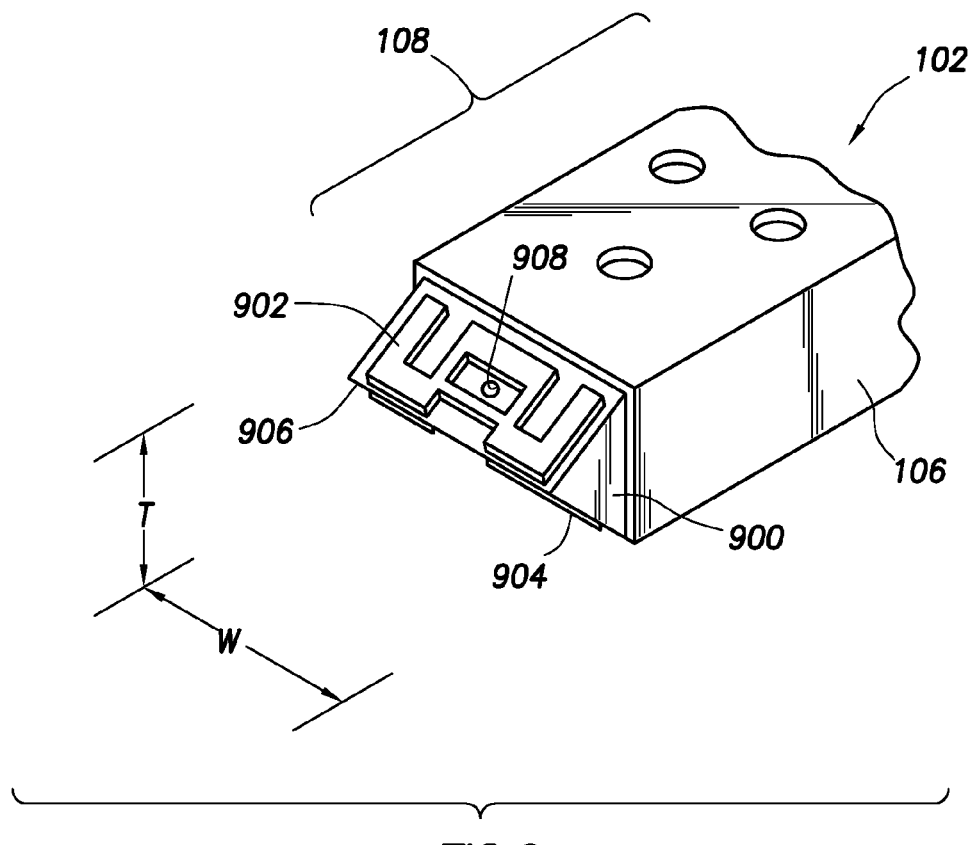
FIG. 9 shows a perspective view of a portion of a wand in accordance with at least some embodiments.

However, while there may be benefits to the "slicing" action of the wire electrodes of FIGS. 2, 3A and 3B, such "slicing" action is not required, and target tissue to be removed may be more fully ablated. FIG. 9 shows the distal end of a wand 102 in accordance with yet still other embodiments. In particular, the distal end 108 defines a width (labeled W in the figure) and a thickness (labeled T in the figure). In some embodiments the elongate shaft 106 is made of a metallic material (e.g., Grade TP304 stainless steel hypodermic tubing). In other embodiments, the elongate shaft may be constructed of other suitable materials, such as inorganic insulating materials. For the reasons discussed with respect to the wand 102 embodiments of FIGS. 3A and 3B, in at least some embodiments the metallic material of the elongate shaft 106 is not electrically grounded or electrically coupled to the generator of the controller 104. The elongate shaft 106 may define a circular cross-section at the handle or proximal end 110 (not shown in FIG. 9), and the distal end 108 may be flattened to define rectangular cross-section. In other embodiments, the flattened portion may define a semi-circular cross section. For wands intended for use in spinal procedures, the width W may be a centimeter or less, and in some cases a 5 millimeters. Likewise, for wands intended use in spinal procedures, the thickness T is 4 millimeters or less, and in some cases 3 millimeters. Other dimensions, particularly larger dimensions, may be equivalently used when the surgical procedure allows.

In embodiments where the elongate shaft is metallic, the distal end 108 may further comprise a non-conductive spacer 900 coupled to the elongate shaft 106. In some cases the spacer 200 is ceramic, but other non-conductive materials resistant to degradation when exposed to plasma may be equivalently used. The spacer 900 supports electrodes of conductive material, with illustrative electrodes labeled 902 and 904 in FIG. 9. In accordance with at least some embodiments, the upper electrode 202 is disposed above a plane that bisects the thickness, and with the lower electrode 204 disposed below the plane that bisects the thickness. Each electrode 902 and 904 defines an exposed surface area of conductive material, and in accordance with at least some embodiments the exposed surface area as between the upper electrode 902 and the lower electrode 904 is the same or substantially the same. In the particular embodiment of FIG. 9, each electrode 902 and 904 is a metallic fixture set at an angle such that the upper electrode 902 slopes towards the distal end 906 of the spacer 900. The exposed surface area for a particular wand depends, at least in part, on the parasitic stimulation of muscle and/or nerves that can be tolerated by the particular medical procedure. Greater parasitic stimulation is present with greater exposed surface area of the electrodes, and less parasitic stimulation is present with less exposed surface area. In embodiments as in FIG. 9, in some cases the exposed surface area of each electrode may range from 0.005 square inches to 0.030 square inches, and in a particular embodiment 0.020 square inches.

In accordance with at least some embodiments, not only do the electrodes define substantially the same exposed surface area as between the upper and lower electrodes, but also the shape as between the upper and lower electrodes is symmetric. In particular, the upper electrode 902 defines a particular shape, and likewise the lower electrode defines a particular shape. The shapes defined by the electrodes 902 and 904 are symmetric about a plane that bisects the thickness T. More particularly still, in some embodiments the electrodes 202 and 204 are mirror images of each other reflected about a plane that bisects the thickness. In other embodiments, the shape of the electrodes may be non-symmetrical, even if the exposed surface areas are substantially the same.

In some embodiments saline is delivered to the distal end 108 of wand, possibly to aid in plasma creation. FIG. 9 illustrates a discharge aperture 908 on the distal end 108 within electrode 902. A similar discharge aperture is present with respect to electrode 904, but is not visible in the view of FIG. 9. While two discharge apertures are contemplated in FIG. 9, a single discharge aperture may be used (e.g., disposed through the distal end 906 of the spacer), and likewise multiple (even non-symmetric) discharge apertures associated with each electrode 902 and 904. The discharge apertures fluidly couple to the flexible tubular member 116 (FIG. 1) by way of a fluid conduit within the wand 102. Thus, saline or other fluid may be pumped into the flexible tubular member 116 (FIG. 1) and discharge through the discharge apertures. In yet still further embodiments, aspiration is provided at the distal end 108 of the wand 102. FIG. 9 illustrates aspiration apertures 220, 222 and 224, which operate similarly to those discussed with respect to FIGS. 3A and 3B.

The embodiments of FIG. 9 operate similarly to the wire loop embodiments in the sense that each electrode 902 and 904 are coupled to the terminals 824 and 826, respectively, and that plasma will be created near the electrode where current density is the greatest. Moreover, the cycling RF energy may extinguish the plasma near one electrode, and enable plasma creation near the other electrode. Unlike the embodiments of FIGS. 3A and 3B, however, the electrodes of FIG. 9 do not necessarily "slice" tissue; rather, the electrodes 902 and 904 of FIG. 9 may be used in situation where the desire is to ablate substantially all tissue that is to be removed.

Figure 10:
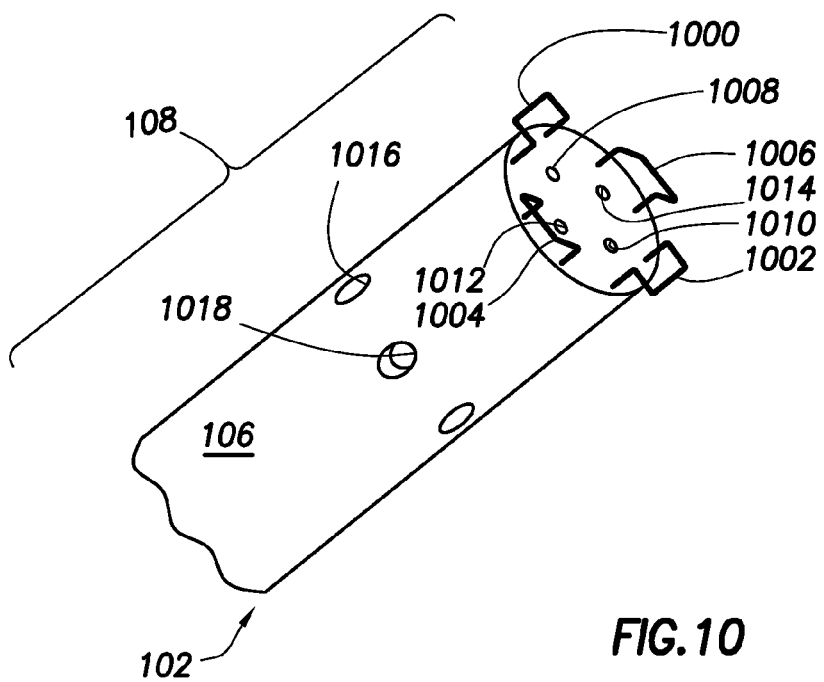
FIG. 10 shows a perspective view of a portion of a wand in accordance with at least some embodiments.

While the various embodiments discussed to this point have all been in relation to wands 102 having two electrodes, in yet still other embodiments more electrodes may be used. For example, FIG. 10 illustrates alternative embodiments of the distal end 108 of a wand 102 with four electrodes. In particular, FIG. 10 illustrates the elongate shaft 106 defining a circular cross-section, even at the distal end. Moreover, the wand 102 has four electrodes 1000, 1002, 1004 and 1006, with each electrodes illustrated as a wire loop electrode (though wire loops are not required). In these embodiments, the electrodes couple in pairs to the terminals of the voltage generator 816 of the controller 104. For example, electrodes 1000 and 1002 may couple to the terminal 824 (FIG. 8), and electrodes 1004 and 1006 may couple to the terminal 826. Thus, plasma may be created proximate to the pair of electrodes that create the highest current density (to become the active electrodes), and the remaining pair will acts a return electrodes, with the designation as active or return changing intermittently as the plasma is re-formed responsive to the generator operation as discussed above.

Moreover, FIG. 10 also illustrates more than two discharge apertures may be used, such as the illustrative four discharge apertures 1008, 1010, 1012 and 1014. Finally, FIG. 10 illustrates aspiration apertures 1016 and 1018, which operate similarly to the aspiration apertures discussed with respect to the other embodiments.

Figure 11:
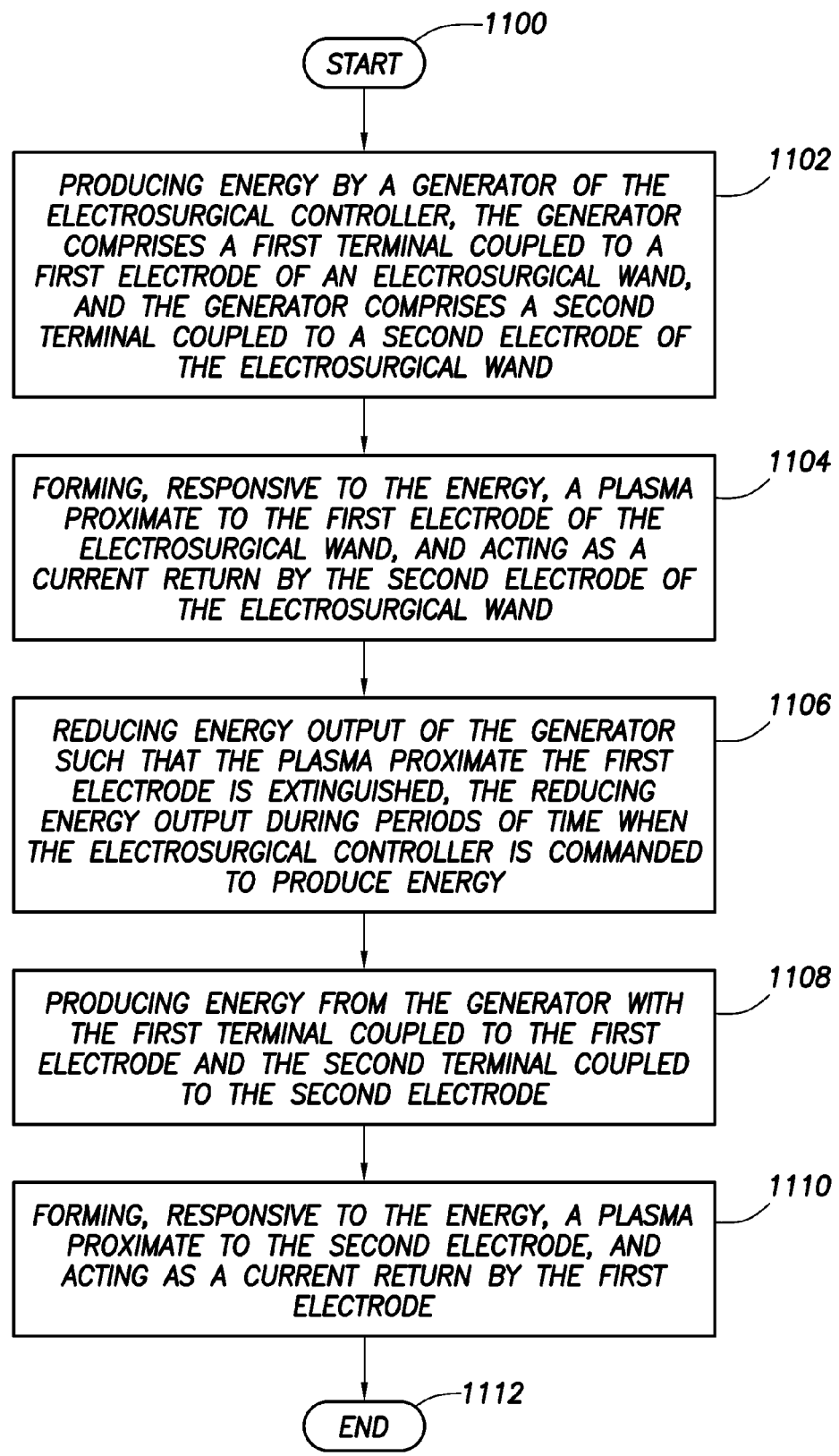
FIG. 11 shows a method in accordance with at least some embodiments.

FIG. 11 shows a method in accordance with at least some embodiments. In particular, the method starts (block 1100) and comprises: producing energy by a generator of the electrosurgical controller, the generator comprises a first terminal coupled to a first electrode of an electrosurgical wand, and the generator comprises a second terminal coupled to a second electrode of the electrosurgical wand (block 1102); forming, responsive to the energy, a plasma proximate to the first electrode of the electrosurgical wand, the second electrode acting as a current return (block 1104); reducing energy output of the generator such that the plasma proximate the first electrode is extinguished, the reducing energy output during periods of time when the electrosurgical controller is commanded to produce energy (block 1106); producing energy from the generator with the first terminal coupled to the first electrode and the second terminal coupled to the second electrode (block 1108); and forming, responsive to the energy, a plasma proximate to the second electrode, and the first electrode acting as a current return (block 1110). And thereafter the method ends (block 1112).

FIG. 12 shows another method in accordance with at least some embodiments. In particular, the method starts (block 1200) and proceeds to treating a disc between vertebrae of a spine (block 1202). The treating the disc is by: inserting an electrosurgical wand to abut a portion of the disc (block 1204); commanding an electrosurgical controller to supply radio frequency energy to electrosurgical wand (block 1206); producing energy by a generator of the electrosurgical controller, the generator comprises a first terminal coupled to a first electrode of the electrosurgical wand, and the generator comprises a second terminal coupled to a second electrode of the electrosurgical wand (block 1208); ablating a portion of the disc by a plasma proximate to the first electrode of the electrosurgical wand, and acting as a current return by the second electrode of the electrosurgical wand (block 1210); reducing energy output of the generator such that the plasma proximate the first electrode is extinguished, the reducing energy output during periods of time when the electrosurgical controller is commanded to produce energy (block 1212); producing energy from the generator with the first terminal coupled to the first electrode and the second terminal coupled to the second electrode (block 1214); and ablating a portion of the disc by a plasma proximate to the second electrode, and acting as a current return by the first electrode (block 1216). Thereafter, the method ends (block 1218).

The above discussion is meant to be illustrative of the principles and various embodiments of the present invention. Numerous variations and modifications possible. For example, while in some cases electrodes were designated as upper electrodes and lower electrodes, such a designation was for purposes of discussion, and shall not be read to require any relationship to gravity during surgical procedures. It is intended that the following claims be interpreted to embrace all such variations and modifications.

While preferred embodiments of this disclosure have been shown and described, modifications thereof can be made by one skilled in the art without departing from the scope or teaching herein. The embodiments described herein are exemplary only and are not limiting. Because many varying and different embodiments may be made within the scope of the present inventive concept, including equivalent structures, materials, or methods hereafter though of, and because many modifications may be made in the embodiments herein detailed in accordance with the descriptive requirements of the law, it is to be understood that the details herein are to be interpreted as illustrative and not in a limiting sense.

What is claimed is:

1. A method of operation of an electrosurgical controller comprising:
    commanding the electrosurgical controller to produce an energy output by a generator of the electrosurgical controller, wherein the generator comprises a first terminal coupled to a first electrode of an electrosurgical wand, and the generator comprises a second terminal coupled to a second electrode of the electrosurgical wand, the first and second electrodes each having a substantially equal surface area;
    applying the energy output across the first and second terminals without favoring delivery of the energy output to one of the first or second electrodes over the other;
    forming, responsive to the energy output, a plasma proximate to the first electrode of the electrosurgical wand, thereby causing the second electrode of the electrosurgical wand to act as a return electrode; and then
    reducing the energy output of the generator such that the plasma proximate the first electrode is extinguished, the step of reducing the energy output occurring without interruption to the step of commanding the electrosurgical controller to produce the energy output; and then
    again producing the energy output by the generator and applying the energy output across the first and second terminals without favoring delivery of the energy output to one of the first or second electrodes over the other; and
    forming, responsive to the energy output and in the absence of a changing command, a plasma proximate to the second electrode, thereby causing the first electrode to act as the return electrode.

2. The method of claim 1 wherein reducing the energy output further comprises turning the generator off for a predetermined period of time.

3. The method of claim 1 wherein reducing the energy output further comprises reducing the energy output for at least 20 milliseconds (ms).

4. The method of claim 3 wherein reducing the energy output further comprises reducing the energy output for 50 ms.

5. The method of claim 1 wherein producing the energy output from the generator further comprises producing the energy output for between and including 50 milliseconds (ms) and 2000 ms.

6. The method of claim 5 wherein producing the energy output from the generator further comprises producing the energy output for 500 ms.

7. The method of claim 1 wherein reducing the energy output further comprises reducing the energy output during a period of time when a foot pedal device, actuation of which indicates the step of commanding the electrosurgical controller to produce the energy output by the generator, is actuated.

8. The method of claim 1 wherein forming the plasma proximate the first electrode, and then forming the plasma proximate the second electrode, occurs in the absence of a command provided to the electrosurgical controller to change an active electrode.

9. The method of claim 1 wherein producing the energy output further comprises producing radio frequency energy.

10. The method of claim 1 wherein forming the plasma proximate to the first electrode further comprises forming the plasma proximate the first electrode, the first electrode being the electrode where the highest current density is formed.

11. The method of claim 1 wherein forming the plasma proximate to the first electrode further comprises forming the plasma proximate the first electrode, the first electrode being the electrode closest to tissue to be treated.

12. The method of claim 1, wherein the steps of producing, reducing and then again producing the energy output are performed automatically by the controller.

13. The method of claim 1, the step of again producing the energy output occurring without change or interruption to the step of commanding the electrosurgical controller.

* * * * *